United States Patent
Westwick et al.

(10) Patent No.: US 10,694,152 B2
(45) Date of Patent: *Jun. 23, 2020

(54) IMAGING SYSTEMS AND METHODS FOR DISPLAYING FLUORESCENCE AND VISIBLE IMAGES

(71) Applicant: Novadaq Technologies ULC, Burnaby (CA)

(72) Inventors: Paul R. Westwick, Vancouver (CA); David Potkins, White Rock (CA); John Fengler, North Vancouver (CA)

(73) Assignee: Novadaq Technologies ULC, Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/343,034

(22) Filed: Nov. 3, 2016

(65) Prior Publication Data

US 2017/0064257 A1  Mar. 2, 2017

Related U.S. Application Data

(63) Continuation of application No. 14/860,687, filed on Sep. 21, 2015, which is a continuation of application
(Continued)

(51) Int. Cl.
*H04N 7/18* (2006.01)
*A61B 3/18* (2006.01)
(Continued)

(52) U.S. Cl.
CPC ............. *H04N 7/183* (2013.01); *A61B 1/041* (2013.01); *A61B 1/043* (2013.01); *A61B 1/045* (2013.01);
(Continued)

(58) Field of Classification Search
CPC ......... A61B 1/041; A61B 1/043; A61B 1/045; A61B 1/051; A61B 1/0638; A61B 1/0646;
(Continued)

(56) References Cited

U.S. PATENT DOCUMENTS 1,290,744 A   1/1919   Hollander
D62,892 S    8/1923   Dinkelspiel
(Continued)

FOREIGN PATENT DOCUMENTS

CN   101726980 A   6/2010
CN   101828139 A   9/2010
(Continued)

OTHER PUBLICATIONS

US 6,692,429 B1, 02/2004, Imaizumi et al. (withdrawn)
(Continued)

*Primary Examiner* — Mohammed S Rahaman
(74) *Attorney, Agent, or Firm* — Morrison & Foerster LLP

(57) ABSTRACT

An endoscopic video system and method using a camera with a single color image sensor, for example a CCD color image sensor, for fluorescence and color imaging and for simultaneously displaying the images acquired in these imaging modes at video rates in real time is disclosed. The tissue under investigation is illuminated continuously with fluorescence excitation light and is further illuminated periodically using visible light outside of the fluorescence excitation wavelength range. The illumination sources may be conventional lamps using filters and shutters, or may include light-emitting diodes mounted at the distal tip of the endoscope.

23 Claims, 10 Drawing Sheets

Related U.S. Application Data

No. 13/930,225, filed on Jun. 28, 2013, now Pat. No. 9,143,746, which is a continuation of application No. 11/964,330, filed on Dec. 26, 2007, now Pat. No. 8,498,695.

(60) Provisional application No. 60/908,373, filed on Mar. 27, 2007, provisional application No. 60/876,597, filed on Dec. 22, 2006.

(51) Int. Cl.
*A61B 1/04* (2006.01)
*A61B 1/045* (2006.01)
*A61B 1/06* (2006.01)
*H04N 5/225* (2006.01)
*H04N 9/04* (2006.01)
*A61B 1/12* (2006.01)
*A61B 1/05* (2006.01)

(52) U.S. Cl.
CPC ............ *A61B 1/051* (2013.01); *A61B 1/0638* (2013.01); *A61B 1/0646* (2013.01); *A61B 1/0669* (2013.01); *A61B 1/0676* (2013.01); *A61B 1/0684* (2013.01); *A61B 1/128* (2013.01); *A61B 3/18* (2013.01); *H04N 5/2256* (2013.01); *H04N 9/045* (2013.01); *H04N 2005/2255* (2013.01)

(58) Field of Classification Search
CPC ... A61B 1/0669; A61B 1/0676; A61B 1/0684; A61B 1/128; A61B 3/18; A61B 5/0071; A61B 1/0005; H04N 2005/2255; H04N 5/2256; H04N 7/183; H04N 9/045; G01J 3/4406; G01N 21/6456
See application file for complete search history.

(56) References Cited

U.S. PATENT DOCUMENTS

| | | |
|---|---|---|
| 2,453,336 A | 11/1948 | Orser |
| 2,857,523 A | 10/1958 | Corso |
| 3,215,029 A | 11/1965 | Woodcock |
| 3,582,178 A | 6/1971 | Boughton et al. |
| 3,671,098 A | 6/1972 | Rotter |
| 3,749,494 A | 7/1973 | Hodges |
| 3,790,248 A | 2/1974 | Kellow |
| 3,931,593 A | 1/1976 | Marshall |
| 3,970,373 A | 7/1976 | Pledger |
| 3,971,068 A | 7/1976 | Gerhardt et al. |
| 4,037,866 A | 7/1977 | Price |
| 4,066,330 A | 1/1978 | Jones |
| 4,115,812 A | 9/1978 | Akatsu |
| 4,149,190 A | 4/1979 | Wessler et al. |
| 4,158,504 A | 6/1979 | de Ponteves et al. |
| 4,200,801 A | 4/1980 | Schuresko |
| 4,260,217 A | 4/1981 | Traeger et al. |
| 4,318,395 A | 3/1982 | Tawara |
| 4,355,325 A | 10/1982 | Nakamura et al. |
| 4,378,571 A | 3/1983 | Handy |
| 4,449,535 A | 5/1984 | Renault |
| 4,471,766 A | 9/1984 | Terayama |
| 4,532,918 A | 8/1985 | Wheeler |
| 4,556,057 A | 12/1985 | Hiruma et al. |
| 4,575,632 A | 3/1986 | Lange |
| 4,597,630 A | 7/1986 | Brandstetter et al. |
| 4,611,888 A | 9/1986 | Prenovitz et al. |
| 4,638,365 A | 1/1987 | Kato |
| 4,656,508 A | 4/1987 | Yokota |
| 4,660,982 A | 4/1987 | Okada |
| 4,688,905 A | 8/1987 | Okamura |
| 4,717,952 A | 1/1988 | Kohayakawa et al. |
| 4,742,388 A | 5/1988 | Cooper et al. |
| 4,768,513 A | 9/1988 | Suzuki |
| 4,786,813 A | 11/1988 | Svanberg et al. |
| 4,799,104 A | 1/1989 | Hosoya et al. |
| 4,806,005 A | 2/1989 | Schneider et al. |
| 4,821,117 A | 4/1989 | Sekiguchi |
| 4,837,625 A | 6/1989 | Douziech et al. |
| 4,852,985 A | 8/1989 | Fujihara et al. |
| 4,856,495 A | 8/1989 | Tohjoh et al. |
| 4,885,634 A | 12/1989 | Yabe |
| 4,895,145 A | 1/1990 | Joffe et al. |
| 4,930,516 A | 6/1990 | Alfano et al. |
| 4,930,883 A | 6/1990 | Salzman |
| 4,951,135 A | 8/1990 | Sasagawa et al. |
| 4,953,539 A | 9/1990 | Nakamura et al. |
| 4,954,897 A | 9/1990 | Ejima et al. |
| 4,974,936 A | 12/1990 | Ams et al. |
| 5,001,556 A | 3/1991 | Nakamura et al. |
| 5,007,408 A | 4/1991 | Ieoka |
| 5,028,128 A | 7/1991 | Onuki |
| 5,034,888 A | 7/1991 | Uehara et al. |
| 5,041,852 A | 8/1991 | Misawa et al. |
| 5,115,308 A | 5/1992 | Onuki |
| 5,121,220 A | 6/1992 | Nakamoto |
| 5,128,803 A | 7/1992 | Sprafke |
| 5,132,837 A | 7/1992 | Kitajima |
| 5,134,662 A | 7/1992 | Bacus et al. |
| 5,159,398 A * | 10/1992 | Maekawa .......... G01N 15/1427 250/461.2 |
| 5,165,079 A | 11/1992 | Schulz-Hennig |
| 5,205,280 A | 4/1993 | Dennison, Jr. et al. |
| 5,208,651 A | 5/1993 | Buican |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,282,082 A | 1/1994 | Espie et al. |
| 5,295,017 A | 3/1994 | Brown |
| RE34,622 E | 5/1994 | Ledley |
| 5,365,057 A | 11/1994 | Morley et al. |
| 5,371,355 A | 12/1994 | Wodecki |
| 5,377,686 A | 1/1995 | O'Rourke et al. |
| 5,379,756 A | 1/1995 | Pileski et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,426,530 A | 6/1995 | Copenhaver et al. |
| 5,430,476 A | 7/1995 | Häfele et al. |
| D362,465 S | 9/1995 | Gallemore |
| 5,481,401 A | 1/1996 | Kita et al. |
| 5,485,203 A | 1/1996 | Nakamura et al. |
| 5,490,015 A | 2/1996 | Umeyama et al. |
| 5,507,287 A | 4/1996 | Palcic et al. |
| 5,515,449 A | 5/1996 | Tsuruoka et al. |
| 5,535,052 A | 7/1996 | Jörgens |
| 5,536,236 A | 7/1996 | Yabe et al. |
| 5,557,451 A | 9/1996 | Copenhaver et al. |
| 5,585,846 A | 12/1996 | Kim |
| 5,590,660 A | 1/1997 | MacAulay et al. |
| 5,596,654 A | 1/1997 | Tanaka |
| 5,646,680 A | 7/1997 | Yajima |
| 5,647,368 A | 7/1997 | Zeng et al. |
| 5,647,840 A | 7/1997 | D'Amelio et al. |
| 5,667,472 A | 9/1997 | Finn et al. |
| 5,677,724 A | 10/1997 | Takizawa et al. |
| 5,682,567 A | 10/1997 | Spruck et al. |
| 5,689,354 A | 11/1997 | Orino |
| 5,695,049 A | 12/1997 | Bauman |
| 5,697,373 A | 12/1997 | Richards-Kortum et al. |
| 5,713,364 A | 2/1998 | DeBaryshe et al. |
| 5,729,382 A | 3/1998 | Morita et al. |
| 5,749,830 A | 5/1998 | Kaneko et al. |
| 5,769,792 A | 6/1998 | Palcic et al. |
| 5,772,355 A | 6/1998 | Ross et al. |
| 5,772,580 A | 6/1998 | Utsui et al. |
| 5,827,190 A | 10/1998 | Palcic et al. |
| 5,833,617 A | 11/1998 | Hayashi |
| 5,838,001 A | 11/1998 | Minakuchi et al. |

(56) References Cited

U.S. PATENT DOCUMENTS

| | | | |
|---|---|---|---|
| 5,840,017 A | 11/1998 | Furuswaba et al. |
| 5,852,498 A | 12/1998 | Youvan et al. |
| 5,891,016 A | 4/1999 | Utsui et al. |
| 5,897,269 A | 4/1999 | Ross et al. |
| 5,971,918 A | 10/1999 | Zanger |
| 5,973,315 A | 10/1999 | Saldana et al. |
| 5,984,861 A | 11/1999 | Crowley |
| 5,986,271 A | 11/1999 | Lazarev et al. |
| 5,986,642 A | 11/1999 | Ueda et al. |
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,622 A | 2/2000 | Suzuki |
| 6,030,339 A | 2/2000 | Tatsuno et al. |
| 6,059,719 A | 5/2000 | Yamamoto et al. |
| 6,059,720 A | 5/2000 | Furusawa et al. |
| 6,061,591 A * | 5/2000 | Freitag .............. A61B 5/0071 600/476 |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,106 A | 8/2000 | MacKinnon et al. |
| 6,120,435 A | 9/2000 | Eino |
| 6,147,705 A | 11/2000 | Krauter et al. |
| 6,148,227 A | 11/2000 | Wagnières et al. |
| 6,161,035 A | 12/2000 | Furusawa |
| 6,181,414 B1 | 1/2001 | Raz et al. |
| 6,192,267 B1 | 2/2001 | Scherninski et al. |
| 6,212,425 B1 | 4/2001 | Irion et al. |
| 6,226,126 B1 | 5/2001 | Conemac |
| 6,258,576 B1 | 7/2001 | Richards-Kortum et al. |
| D446,524 S | 8/2001 | Bontly et al. |
| 6,280,378 B1 | 8/2001 | Kazuhiro et al. |
| 6,293,911 B1 | 9/2001 | Imaizumi et al. |
| 6,315,712 B1 | 11/2001 | Rovegno |
| 6,332,092 B1 | 12/2001 | Deckert et al. |
| 6,364,829 B1 | 4/2002 | Fulghum |
| 6,364,831 B1 | 4/2002 | Crowley |
| D456,809 S | 5/2002 | Schieffers |
| 6,419,628 B1 | 7/2002 | Rudischhauser et al. |
| 6,422,994 B1 | 7/2002 | Kaneko et al. |
| 6,462,770 B1 | 10/2002 | Cline et al. |
| 6,510,338 B1 | 1/2003 | Irion et al. |
| 6,526,213 B1 | 2/2003 | Ilenda et al. |
| 6,529,239 B1 | 3/2003 | Dyck et al. |
| 6,529,768 B1 | 3/2003 | Hakamata |
| 6,537,211 B1 | 3/2003 | Wang et al. |
| 6,544,102 B2 | 4/2003 | Schäfer et al. |
| 6,571,119 B2 | 5/2003 | Hayashi |
| 6,596,996 B1 | 7/2003 | Stone et al. |
| 6,603,552 B1 | 8/2003 | Cline et al. |
| 6,639,664 B2 | 10/2003 | Haan et al. |
| 6,652,452 B1 | 11/2003 | Seifert et al. |
| 6,750,971 B2 | 6/2004 | Overbeck et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,826,424 B1 | 11/2004 | Zeng et al. |
| 6,898,458 B2 | 5/2005 | Zeng et al. |
| 6,899,675 B2 | 5/2005 | Cline et al. |
| 6,922,583 B1 | 7/2005 | Perelman et al. |
| 6,958,862 B1 | 10/2005 | Joseph |
| 6,960,165 B2 | 11/2005 | Ueno et al. |
| 7,043,291 B2 | 5/2006 | Sendai |
| D524,985 S | 7/2006 | Lukan et al. |
| D524,987 S | 7/2006 | Lukan et al. |
| 7,150,552 B2 | 12/2006 | Weidel |
| 7,179,222 B2 | 2/2007 | Imaizumi et al. |
| 7,235,045 B2 | 6/2007 | Wang et al. |
| 7,236,815 B2 | 6/2007 | Richards-Kortum et al. |
| 7,253,894 B2 | 8/2007 | Zeng et al. |
| 7,324,674 B2 | 1/2008 | Ozawa et al. |
| 7,333,270 B1 | 2/2008 | Pochapsky et al. |
| 7,341,557 B2 | 3/2008 | Cline et al. |
| 7,385,772 B2 | 6/2008 | Forkey et al. |
| 7,420,151 B2 | 9/2008 | Fengler et al. |
| 7,479,990 B2 | 1/2009 | Imaizumi et al. |
| D599,799 S | 9/2009 | Di Bari et al. |
| D603,408 S | 11/2009 | Fitch |
| D606,544 S | 12/2009 | Di Bari et al. |
| 7,697,975 B2 | 4/2010 | Zeng |
| 7,704,206 B2 | 4/2010 | Suzuki et al. |
| 7,722,534 B2 | 5/2010 | Cline et al. |
| 7,777,191 B2 | 8/2010 | Olcott et al. |
| 7,798,955 B2 | 9/2010 | Ishihara et al. |
| 7,811,229 B2 | 10/2010 | Sugimoto |
| 7,928,352 B2 | 4/2011 | Toda |
| 8,035,067 B2 | 10/2011 | Toda |
| D653,811 S | 2/2012 | BenZion |
| 8,140,147 B2 | 3/2012 | Maynard et al. |
| 8,285,015 B2 | 10/2012 | Demos |
| 8,337,400 B2 | 12/2012 | Mizuyoshi |
| 8,361,775 B2 | 1/2013 | Flower |
| D677,258 S | 3/2013 | Mistkawi |
| 8,408,269 B2 | 4/2013 | Fengler et al. |
| 8,408,772 B2 | 4/2013 | Li |
| D682,277 S | 5/2013 | Tasselli et al. |
| 8,448,867 B2 | 5/2013 | Liu et al. |
| 8,473,035 B2 | 6/2013 | Frangioni |
| 8,498,695 B2 | 7/2013 | Westwick et al. |
| D692,004 S | 10/2013 | Man |
| 8,630,698 B2 | 1/2014 | Fengler et al. |
| 8,721,532 B2 | 5/2014 | Takei et al. |
| 8,736,748 B2 | 5/2014 | Takita |
| 8,759,243 B2 | 6/2014 | Coffy et al. |
| 8,773,756 B2 | 7/2014 | Tesar et al. |
| 8,790,253 B2 | 7/2014 | Sunagawa et al. |
| 8,830,339 B2 | 9/2014 | Velarde et al. |
| D719,574 S | 12/2014 | Alegiani et al. |
| 8,961,403 B2 | 2/2015 | Cline et al. |
| D723,563 S | 3/2015 | Alegiani |
| 8,979,301 B2 | 3/2015 | Moore |
| D726,186 S | 4/2015 | Jenkins et al. |
| D734,339 S | 7/2015 | Zhou et al. |
| 9,125,552 B2 | 9/2015 | Dunki-Jacobs et al. |
| 9,143,746 B2 | 9/2015 | Westwick et al. |
| 9,173,554 B2 | 11/2015 | Fengler et al. |
| 9,282,305 B2 | 3/2016 | Kikuchi |
| 9,294,691 B2 | 3/2016 | Ooki |
| 9,295,392 B2 | 3/2016 | Douplik et al. |
| 9,386,909 B2 | 7/2016 | Fengler et al. |
| 9,407,838 B2 | 8/2016 | Butte et al. |
| 9,435,496 B2 | 9/2016 | Moore |
| 9,577,012 B2 | 2/2017 | Ooki |
| 9,642,532 B2 | 5/2017 | Fengler et al. |
| D791,137 S | 7/2017 | Wang et al. |
| 9,814,378 B2 | 11/2017 | Moore |
| D815,928 S | 4/2018 | Rummel et al. |
| D826,234 S | 8/2018 | Zhou et al. |
| D835,284 S | 12/2018 | Barker et al. |
| D835,285 S | 12/2018 | Barker et al. |
| 10,356,334 B2 | 7/2019 | Moore et al. |
| 2001/0016679 A1 | 8/2001 | Futatsugi et al. |
| 2001/0028458 A1 | 10/2001 | Xiao |
| 2001/0049473 A1 * | 12/2001 | Hayashi ............ A61B 1/00009 600/317 |
| 2002/0013937 A1 | 1/2002 | Ostanevich et al. |
| 2002/0016533 A1 | 2/2002 | Marchitto et al. |
| 2002/0021355 A1 | 2/2002 | Utsui et al. |
| 2002/0035330 A1 | 3/2002 | Cline et al. |
| 2002/0076480 A1 | 6/2002 | Hsieh et al. |
| 2002/0138008 A1 | 9/2002 | Tsujita et al. |
| 2002/0143243 A1 | 10/2002 | Geordakoudi et al. |
| 2002/0148902 A1 | 10/2002 | Schlieffers |
| 2002/0155619 A1 | 10/2002 | Kurihara et al. |
| 2002/0156380 A1 | 10/2002 | Feld et al. |
| 2002/0161282 A1 * | 10/2002 | Fulghum ............ A61B 1/00009 600/160 |
| 2002/0161283 A1 | 10/2002 | Sendai |

(56) References Cited

U.S. PATENT DOCUMENTS

| | | |
|---|---|---|
| 2002/0161284 A1 | 10/2002 | Tanaka |
| 2002/0168096 A1* | 11/2002 | Hakamata ............... G06T 5/50 382/132 |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2002/0196335 A1 | 12/2002 | Ozawa |
| 2003/0002036 A1 | 1/2003 | Haan et al. |
| 2003/0042493 A1 | 3/2003 | Kazakevich |
| 2003/0063398 A1 | 4/2003 | Abe et al. |
| 2003/0080193 A1 | 5/2003 | Ryan et al. |
| 2003/0117491 A1 | 6/2003 | Avni et al. |
| 2003/0135092 A1 | 7/2003 | Cline et al. |
| 2003/0153811 A1 | 8/2003 | Muckner |
| 2003/0158470 A1* | 8/2003 | Wolters ............... A61B 1/043 600/317 |
| 2003/0191368 A1 | 10/2003 | Wang et al. |
| 2003/0229270 A1 | 12/2003 | Suzuki et al. |
| 2004/0006276 A1 | 1/2004 | Demos et al. |
| 2004/0010183 A1 | 1/2004 | Dhindsa |
| 2004/0020990 A1 | 2/2004 | Haven et al. |
| 2004/0021859 A1 | 2/2004 | Cunningham |
| 2004/0037454 A1 | 2/2004 | Ozawa et al. |
| 2004/0044275 A1 | 3/2004 | Hakamata |
| 2004/0046865 A1 | 3/2004 | Ueno et al. |
| 2004/0133073 A1 | 7/2004 | Berci et al. |
| 2004/0134990 A1 | 7/2004 | Fitch et al. |
| 2004/0143162 A1 | 7/2004 | Krattiger et al. |
| 2004/0148141 A1 | 7/2004 | Tsujita et al. |
| 2004/0149998 A1 | 8/2004 | Henson et al. |
| 2004/0156124 A1 | 8/2004 | Okada |
| 2004/0186351 A1* | 9/2004 | Imaizumi ........... A61B 1/00009 600/160 |
| 2004/0218115 A1 | 11/2004 | Kawana et al. |
| 2004/0225222 A1* | 11/2004 | Zeng ............... A61B 1/043 600/476 |
| 2004/0245350 A1 | 12/2004 | Zeng |
| 2004/0263643 A1 | 12/2004 | Imaizumi et al. |
| 2005/0027166 A1 | 2/2005 | Matsumoto et al. |
| 2005/0096505 A1 | 5/2005 | Imaizumi et al. |
| 2005/0140270 A1 | 6/2005 | Henson et al. |
| 2005/0143627 A1 | 6/2005 | Cline et al. |
| 2005/0154319 A1 | 7/2005 | Cline et al. |
| 2005/0171440 A1 | 8/2005 | Maki et al. |
| 2005/0182291 A1 | 8/2005 | Hirata |
| 2005/0182321 A1 | 8/2005 | Frangioni |
| 2005/0203421 A1 | 9/2005 | Zeng et al. |
| 2005/0256373 A1 | 11/2005 | Bar-Or et al. |
| 2005/0273011 A1 | 12/2005 | Hattery et al. |
| 2005/0280783 A1 | 12/2005 | Yamasaki et al. |
| 2005/0288593 A1 | 12/2005 | Geordakoudi et al. |
| 2006/0002141 A1 | 1/2006 | Ouderkirk et al. |
| 2006/0004292 A1 | 1/2006 | Beylin |
| 2006/0017913 A1 | 1/2006 | Kawamata et al. |
| 2006/0089554 A1 | 4/2006 | Ishihara et al. |
| 2006/0094109 A1 | 5/2006 | Trainer |
| 2006/0146322 A1 | 7/2006 | Komachi et al. |
| 2006/0149133 A1 | 7/2006 | Sugimoto et al. |
| 2006/0155166 A1 | 7/2006 | Takahashi et al. |
| 2006/0211915 A1 | 9/2006 | Takeuchi et al. |
| 2006/0215406 A1 | 9/2006 | Thrailkill |
| 2006/0217594 A1 | 9/2006 | Ferguson |
| 2006/0241496 A1 | 10/2006 | Fengler et al. |
| 2006/0247537 A1 | 11/2006 | Matsumoto |
| 2006/0250696 A1 | 11/2006 | McGuire |
| 2006/0258910 A1 | 11/2006 | Stefanchik et al. |
| 2007/0041195 A1 | 2/2007 | Chen |
| 2007/0091634 A1 | 4/2007 | Sakurada |
| 2007/0177152 A1 | 8/2007 | Tearney et al. |
| 2007/0203413 A1 | 8/2007 | Frangioni |
| 2007/0213593 A1 | 9/2007 | Nakaoka |
| 2007/0229309 A1 | 10/2007 | Tomita et al. |
| 2008/0021274 A1 | 1/2008 | Bayer et al. |
| 2008/0024868 A1 | 1/2008 | Okamura |
| 2008/0027280 A1 | 1/2008 | Fengler et al. |
| 2008/0039697 A1 | 2/2008 | Morishita |
| 2008/0074752 A1 | 3/2008 | Chaves et al. |
| 2008/0177140 A1 | 7/2008 | Cline et al. |
| 2008/0208006 A1 | 8/2008 | Farr |
| 2008/0217411 A1 | 9/2008 | Ledwith et al. |
| 2008/0246920 A1 | 10/2008 | Buczek et al. |
| 2009/0012361 A1 | 1/2009 | MacKinnon et al. |
| 2009/0021739 A1 | 1/2009 | Tsujita et al. |
| 2009/0036734 A1 | 2/2009 | Dunki-Jacobs et al. |
| 2009/0040754 A1 | 2/2009 | Brukilacchio et al. |
| 2009/0052185 A1 | 2/2009 | Toriyama et al. |
| 2009/0114799 A1 | 5/2009 | Maeda |
| 2009/0114803 A1 | 5/2009 | Yamaguchi |
| 2009/0122135 A1 | 5/2009 | Matsui |
| 2009/0122152 A1 | 5/2009 | Yamaguchi et al. |
| 2009/0124854 A1 | 5/2009 | Yamaguchi et al. |
| 2009/0153797 A1 | 6/2009 | Allon et al. |
| 2009/0181339 A1 | 7/2009 | Liang et al. |
| 2009/0201577 A1 | 8/2009 | LaPlante et al. |
| 2009/0218405 A1 | 9/2009 | Joseph et al. |
| 2009/0290149 A1 | 11/2009 | Roth |
| 2010/0065641 A1 | 3/2010 | Liu et al. |
| 2010/0087741 A1 | 4/2010 | Douplik et al. |
| 2010/0094136 A1 | 4/2010 | Nakaoka et al. |
| 2010/0110168 A1 | 5/2010 | Avni et al. |
| 2010/0110393 A1 | 5/2010 | Chen et al. |
| 2010/0121146 A1 | 5/2010 | Sugimoto |
| 2010/0125164 A1 | 5/2010 | LaBombard |
| 2010/0155487 A1 | 6/2010 | Liu et al. |
| 2010/0157039 A1 | 6/2010 | Sugai |
| 2010/0168588 A1 | 7/2010 | Matsumoto et al. |
| 2010/0198010 A1 | 8/2010 | Cline et al. |
| 2010/0208487 A1 | 8/2010 | Li |
| 2010/0277817 A1 | 11/2010 | Durell |
| 2010/0308116 A1 | 12/2010 | Sani et al. |
| 2011/0032350 A1 | 2/2011 | Kikuchi et al. |
| 2011/0073658 A1 | 3/2011 | Vassura et al. |
| 2011/0235017 A1 | 9/2011 | Iwasaki |
| 2011/0244506 A1 | 10/2011 | Sutter et al. |
| 2011/0270092 A1 | 11/2011 | Kang et al. |
| 2011/0290889 A1 | 12/2011 | Tamburini et al. |
| 2012/0006897 A1 | 1/2012 | Barkan et al. |
| 2012/0044462 A1 | 2/2012 | Kaji |
| 2012/0150046 A1 | 6/2012 | Watson et al. |
| 2012/0256002 A1 | 10/2012 | O'Donnell et al. |
| 2012/0319645 A1 | 12/2012 | O'Donnell et al. |
| 2013/0008964 A1 | 1/2013 | Hawley et al. |
| 2013/0237762 A1 | 9/2013 | Fengler et al. |
| 2014/0071328 A1 | 3/2014 | Miesak |
| 2014/0078378 A1 | 3/2014 | Demers et al. |
| 2014/0139893 A1 | 5/2014 | Sugiyama et al. |
| 2014/0187967 A1 | 7/2014 | Wood et al. |
| 2014/0194687 A1 | 7/2014 | Fengler et al. |
| 2015/0184811 A1 | 7/2015 | Moore |
| 2015/0230698 A1 | 8/2015 | Cline et al. |
| 2015/0320296 A1 | 11/2015 | Morita |
| 2015/0381909 A1 | 12/2015 | Butte et al. |
| 2016/0041098 A1 | 2/2016 | Hirawake et al. |
| 2016/0044253 A1 | 2/2016 | Dainty et al. |
| 2016/0100763 A1 | 4/2016 | Fengler et al. |
| 2016/0249019 A1 | 8/2016 | Westwick et al. |
| 2016/0360956 A1 | 12/2016 | Moore |
| 2017/0064258 A1 | 3/2017 | Westwick et al. |
| 2017/0142314 A1 | 5/2017 | Moore et al. |
| 2017/0167980 A1 | 6/2017 | Dimitriadis et al. |
| 2017/0209050 A1 | 7/2017 | Fengler et al. |
| 2017/0273567 A1 | 9/2017 | Fengler et al. |
| 2017/0354392 A1 | 12/2017 | Fengler et al. |

FOREIGN PATENT DOCUMENTS

| | | |
|---|---|---|
| CN | 201974160 U | 9/2011 |
| DE | 19535114 A1 | 3/1996 |
| DE | 19608027 A1 | 9/1996 |
| EP | 0512965 A1 | 11/1992 |
| EP | 0672379 A1 | 9/1995 |
| EP | 0774865 A2 | 5/1997 |
| EP | 0792618 A1 | 9/1997 |
| EP | 0671706 B1 | 6/1999 |

(56) References Cited

FOREIGN PATENT DOCUMENTS

| | | |
|---|---|---|
| EP | 1374755 A1 | 1/2004 |
| EP | 1883337 A1 | 2/2008 |
| EP | 2051603 A1 | 4/2009 |
| EP | 2859837 A1 | 4/2015 |
| FR | 2671405 A1 | 7/1992 |
| JP | S60-246733 A | 12/1985 |
| JP | S61-159936 A | 7/1986 |
| JP | H-01-135349 A | 5/1989 |
| JP | 03-97439 A | 4/1991 |
| JP | 03-97441 A | 4/1991 |
| JP | 03-97442 A | 4/1991 |
| JP | 05-115435 A | 5/1993 |
| JP | 06-125911 A | 5/1994 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | H07-204156 A | 8/1995 |
| JP | H07-222712 A | 8/1995 |
| JP | H07-250804 A | 10/1995 |
| JP | H07-250812 A | 10/1995 |
| JP | H07-327913 A | 12/1995 |
| JP | H08-126605 A | 5/1996 |
| JP | 08-140928 A2 | 6/1996 |
| JP | 08-140929 A2 | 6/1996 |
| JP | H08-224208 A | 9/1996 |
| JP | H08-224209 A | 9/1996 |
| JP | H08-224210 A | 9/1996 |
| JP | H08-224240 A | 9/1996 |
| JP | H08-252218 A | 10/1996 |
| JP | H09-19408 A | 1/1997 |
| JP | 09-066023 A2 | 3/1997 |
| JP | 09-070384 A2 | 3/1997 |
| JP | H10-127563 A | 5/1998 |
| JP | H10-151104 A | 6/1998 |
| JP | 10-225427 A2 | 8/1998 |
| JP | H10-201700 A | 8/1998 |
| JP | H10-201707 A | 8/1998 |
| JP | H10-225426 A | 8/1998 |
| JP | H10-24320 A | 9/1998 |
| JP | H10-243915 A | 9/1998 |
| JP | H10-308114 A | 11/1998 |
| JP | H10-309281 A | 11/1998 |
| JP | H10-309282 A | 11/1998 |
| JP | H10-321005 A | 12/1998 |
| JP | H10-328129 A | 12/1998 |
| JP | H11-47079 A | 2/1999 |
| JP | 11-089789 A2 | 4/1999 |
| JP | H11-104059 A | 4/1999 |
| JP | H11-104060 A | 4/1999 |
| JP | H11-104061 A | 4/1999 |
| JP | H11-104070 A | 4/1999 |
| JP | H11-113839 A | 4/1999 |
| JP | H11-155812 A | 6/1999 |
| JP | H11-244220 A | 9/1999 |
| JP | H11-332819 A | 12/1999 |
| JP | 2000-504968 A | 4/2000 |
| JP | 2000-245693 A | 9/2000 |
| JP | 2000-354583 A | 12/2000 |
| JP | 2001-78205 A | 3/2001 |
| JP | 2002-000560 A | 1/2002 |
| JP | 02-049302 A | 2/2002 |
| JP | 2002-244122 A | 8/2002 |
| JP | 2003-045210 A | 2/2003 |
| JP | 2004-024611 A | 1/2004 |
| JP | 2004-094043 A | 3/2004 |
| JP | 2004-163902 A | 6/2004 |
| JP | 2004-520105 A | 7/2004 |
| JP | 2004-247156 A | 9/2004 |
| JP | 2004-289545 A | 10/2004 |
| JP | 2004-292722 A | 10/2004 |
| JP | 2005-010315 A | 1/2005 |
| JP | 2005-058618 A2 | 3/2005 |
| JP | 2005-058619 A2 | 3/2005 |
| JP | 2005-058620 A2 | 3/2005 |
| JP | 2005-080819 A2 | 3/2005 |
| JP | 2005-081079 A2 | 3/2005 |
| JP | 2005-149996 A | 6/2005 |
| JP | 2005-292404 A | 10/2005 |
| JP | 2006-003103 A | 1/2006 |
| JP | 2006-073767 A | 3/2006 |
| JP | 2006-087764 A | 4/2006 |
| JP | 2006-525494 A | 11/2006 |
| JP | 2007-029453 A | 2/2007 |
| JP | 2007-072392 A | 3/2007 |
| JP | 2007-089840 A | 4/2007 |
| JP | 2009-259703 A | 11/2009 |
| JP | 2010-107751 A | 5/2010 |
| JP | 2010-117442 A | 5/2010 |
| JP | 2010-524194 A | 7/2010 |
| JP | 2011-500921 A | 1/2011 |
| JP | 2011-072424 A | 4/2011 |
| JP | 2011-169819 A | 9/2011 |
| JP | 2011-528918 A | 12/2011 |
| JP | 5231625 B2 | 7/2013 |
| JP | 2014-123941 A | 7/2014 |
| JP | 5859578 B2 | 2/2016 |
| RU | 99592 U1 | 11/2010 |
| WO | WO-1993/04648 A1 | 3/1993 |
| WO | WO-1994/13191 A1 | 6/1994 |
| WO | WO-1995/26673 A2 | 10/1995 |
| WO | WO-1998/24360 A1 | 6/1998 |
| WO | WO-1999/01749 A1 | 1/1999 |
| WO | WO-1999/53832 A1 | 10/1999 |
| WO | WO-2000/42910 A1 | 7/2000 |
| WO | WO-2000/54652 A1 | 9/2000 |
| WO | WO-2002/007587 A2 | 1/2002 |
| WO | WO-2002/50518 A2 | 6/2002 |
| WO | WO-2003/059159 A2 | 7/2003 |
| WO | WO-2003/059159 A8 | 7/2003 |
| WO | WO-2006/116847 A1 | 11/2006 |
| WO | WO-2007/081707 A2 | 7/2007 |
| WO | WO-2008/011722 A1 | 1/2008 |
| WO | WO-2008/071240 A1 | 6/2008 |
| WO | WO-2009/033021 A2 | 3/2009 |
| WO | WO-2013/160279 A1 | 10/2013 |
| WO | WO-2014/176375 A2 | 10/2014 |
| WO | WO-2016/055837 A1 | 4/2016 |

OTHER PUBLICATIONS

Lyon, R.E. et al. (2002). "Eyeing the Camera: Into the Next Century," *10 Color and Imaging Conference Final Program & Proceedings* 349-355.

Chinese Notice of Allowance dated Jun. 19, 2017 for Chinese Application No. 201280022284.3, filed on Nov. 7, 2013, four pages.

European Communication Pursuant to Article 94(3) EPC dated Apr. 13, 2017, filed on Oct. 4, 2013, five pages.

European Decision to Grant a European Patent Pursuant to Article 97(1) EPC dated Jun. 22, 2017, for EP Application No. 08706262.6 filed on Aug. 21, 2009, two pages.

European Invitation Pursuant to Article 94(3) and Rule 71(1) EPC dated Apr. 6, 2017, for EP Application No. 09819758.5, filed on May 4, 2011, five pages.

International Search Report and Written Opinion dated Sep. 18, 2017, for International Application No. PCT/CA2017/050734, filed on Jun. 14, 2017, eight pages.

Japanese Notice of Allowance dated Nov. 17, 2017, for Japanese Patent Application No. 2016-253736 filed on Dec. 27, 2016, six pages.

Korean Decision on the Trial Against Final Rejection from the Intellectual Property Tribunal (IPT) dated Sep. 25, 2017, for Korean Patent Application No. 2013-7026479, filed on Oct. 7, 2013, seventeen pages.

Korean Notice of Allowance dated Dec. 13, 2017 for Korean Patent Application No. 10-2017-7008654, filed on Mar. 29, 2017, three pages.

Korean Office Action dated Jun. 27, 2017 for Korean Patent Application No. 2017-7008654, filed on Mar. 29, 2017, ten pages.

(56) References Cited

OTHER PUBLICATIONS

U.S. Final Office Action dated Aug. 7, 2017, for U.S. Appl. No. 15/343,038, filed Nov. 3, 2016, eleven pages.
U.S. Non Final Office Action dated Sep. 25, 2017, for U.S. Appl. No. 15/584,405, filed May 2, 2017, eight pages.
U.S. Final Office Action dated Aug. 11, 2017, for U.S. Appl. No. 14/860,687, filed Sep. 21, 2015, seventeen pages.
U.S. Notice of Allowance dated Jul. 10, 2017 for U.S. Appl. No. 15/247,419, filed Aug. 25, 2016, eight pages.
Alfano, R.R. et al. (Oct. 1987). "Fluorescence Spectra From Cancerous and Normal Human Breast and Lung Tissues," *IEEE Journal of Quantum Electronics* QE-23(10):1806-1811.
Andersson-Engels, S. et al. (Mar. 1989). "Tissue Diagnostics Using Laser Induced Fluorescence," *Ber. Bunsenges Physical Chemistry* 93(3):335-342.
Bhunchet, E. et al. (Apr. 2002). "Fluorescein Electronic Endoscopy: A Novel Method for Detection of Early Stage Gastric Cancer Not Evident to Routine Endoscopy," *Gastrointestinal Endoscopy* 55(4):562-571.
Dawson, J.B. et al. (Jul. 1980). "A Theoretical and Experimental Study of Light Absorption and Scattering by In Vivo Skin," *Phys. Med. Biol.* 25(4):695-709.
Georgakoudi, I et al. (2003). "Quantitative Characterization of Biological Tissue Using Optical Spectroscopy," in Chapter 31 of *Biomedical Photonics Handbook*, Tuan Vo-Dinh (ed.), CRC Press, New York, thirty three pages.
Georgakoudi, I et al. (Apr. 2005). "Characterization of Dysplastic Tissue Morphology and Biochemistry in Barrett's Esophagus using Diffuse Reflectance and Light Scattering Spectroscopy," *Techniques in Gastrointestinal Endoscopy* 7(2):100-105.
Hung, J. et al. (1991). "Autofluorescence of Normal and Malignant Bronchial Tissue," *Lasers in Surgery and Medicine* 11(2):99-105.
Török, B. et al. (May 1996). "Simultane digitale Indocyaningrün- und Fluoreszeinangiographie (Simultaneous Digital ICG and Fluorescein Angiography)," *Klin Monatsbl Augenheilkd* 208(5):333-336, (with English Translation of the Introduction).
Canadian Examiner's Report for Registration of an Industrial Design dated Feb. 1, 2017 for Canadian Application No. 171282, filed on Oct. 27, 2016, two pages.
Chinese Office action dated Jul. 29, 2016 for application No. 2012800222843 filed on Mar. 8, 2012, eight pages.
Chinese Office action dated Nov. 24, 2015 for application No. 2012800222843 filed on Mar. 8, 2012, sixteen pages.
Chinese Third Office Action dated Mar. 14, 2017 for Chinese Patent Application No. 201280022284.3, filed on Nov. 7, 2013, seven pages.
European Communication pursuant to Rules 70(2) and 70a(2) EPC and Reference to Rule 39(1) EPC dated Jan. 23, 2017 for European Application No. 16186321.2 filed on Aug. 30, 2016, two pages.
European Communication under Rule 71(3) EPC dated Nov. 25, 2016 for EP Application No. 08706262.6 filed on Aug. 21, 2009, eight pages.
European Extended Search Report dated Jul. 17, 2014, for EP Application No. 09721252.6 filed Mar. 18, 2009; eleven pages.
European Extended Search Report dated Sep. 20, 2013, for EP Application No. 08706262.6 filed on Jan. 23, 2008, five pages.
European Office Action dated Dec. 3, 2015, for EP Application No. 08706262.6 filed on Jan. 23, 2008; fifteen pages.
European Office Action dated Nov. 19, 2015, for EP Application No. 07 785 001.4, filed on Jul. 30, 2007, four pages.
European Office Action dated Nov. 3, 2015 for EP Patent Application No. 12754208.2 filed Oct. 4, 2013, four pages.
European Office Action dated Sep. 29, 2015, for EP Application No. 09721252.6 filed Mar. 18, 2009; five pages.
European Search Report and Written Opinion dated Dec. 21, 2016 for European Application No. 16186321.2 filed on Aug. 30, 2016, nine pages.
European Supplemental Search Report dated Jan. 24, 2012, for European Patent Application No. 07785001.4 filed on Jul. 30, 2007, seven pages.
European Supplemental Search Report dated Oct. 1, 2014 for EP Application No. 12754208.2 filed on Mar. 8, 2012, five pages.
European Supplemental Search Report dated Oct. 9, 2013, for European Patent Application No. 06721854.5, filed on May 4, 2005, six pages.
Extended European Search Report dated Jan. 24, 2012 for EP Application No. 07 785 001.4, filed on Jul. 30, 2007, seven pages.
International Preliminary Report on Patentability dated Feb. 3, 2009, for International Application No. PCT/CA2007/001335 filed on Jul. 30, 2007, five pages.
International Preliminary Report on Patentability dated Nov. 6, 2007, for International Application No. PCT/CA2006/000669, filed on Apr. 27, 2006, nine pages.
International Preliminary Report on Patentability dated Sep. 21, 2010, for International Application No. PCT/US2009/037506, filed on Mar. 18, 2009, seven pages.
International Search Report and written Opinion dated Apr. 24, 2017, for International Application No. PCT/CA2017/050083, filed on Jan. 26, 2017, seven pages.
International Search Report and written Opinion of the International Searching Authority dated Feb. 10, 2017, for International Application No. PCT/CA2016/051315 filed on Nov. 10, 2016, thirteen pages.
International Search Report dated Aug. 3, 2006, for International Application No. PCT/CA2006/000669, filed on Apr. 27, 2006, three pages.
International Search Report dated Aug. 3, 2012, for International Application No. PCT/IB2012/000601, filed on Mar. 8, 2012, three pages.
International Search Report dated Dec. 7, 2007, for International Application No. PCT/CA2007/001335, filed on Jul. 30, 2007, two pages.
International Search Report dated Jan. 21, 2002, for International Application No. PCT/US2001/022198, filed on Jul. 13, 2001, three pages.
International Search Report dated Jul. 22, 2009, for International Application No. PCT/US09/37506, filed on Mar. 18, 2009, two pages.
International Search Report dated May 13, 2008 for Intentional Application No. PCT/CA2008/00015, filed on Jan. 8, 2008, one page.
Invitation to Pay additional Fees and, where Applicable, Protest Fee, dated Dec. 22, 2016 for International Application No. PCT/CA2016/051315, filed on Nov. 10, 2016, two pages.
Japanese Final Office Action dated Aug. 2, 2013, for Japanese Patent Application No. 2008-509275, filed on Apr. 27, 2006, four pages.
Japanese Notice of Allowance dated Jan. 5, 2017 in Japanese Patent Application No. 2015-238784, filed on Dec. 7, 2015, six pages.
Japanese Notice of Allowance dated Nov. 28, 2016 for Japanese Patent Application No. 2015-245598, filed on Mar. 8, 2012, six pages.
Japanese Office Action dated Apr. 20, 2012, issued in counterpart Japanese Application No. 2011-500921, filed Mar. 18, 2009, four pages.
Japanese Office Action dated Apr. 3, 2015 in Japanese Application No. 2013-058356, filed Mar. 18, 2009, four pages.
Japanese Office Action dated Feb. 17, 2012, for Japanese Patent Application No. 2008-509275, filed on Apr. 27, 2006, six pages.
Japanese Office Action dated Jul. 22, 2014 for Japanese Patent Application No. 2013-557187 filed Mar. 8, 2012, seven pages.
Japanese Office Action dated Mar. 9, 2015 for Japanese Patent Application No. 2013-557187, filed Mar. 8, 2012, five pages.
Japanese Office Action dated Nov. 11, 2011, for Japanese Patent Application No. 2009-521077, filed on Jul. 30, 2007, four pages.
Japanese Office Action dated Sep. 14, 2012, for Japanese Patent Application No. 2008-509275, filed on Apr. 27, 2006, seven pages.
Japanese Office Action dated Sep. 19, 2014, for Japanese Patent Application No. 2013-246636, filed on Apr. 27, 2006, six pages.
Japanese Office dated Dec. 26, 2012 for Japanese Patent Application No. 2011-500921, filed on Mar. 18, 2009, two pages.

(56) References Cited

OTHER PUBLICATIONS

Japanese Patent Office Action dated May 26, 2014 in Japanese Patent Application No. 2013-058356, filed on Mar. 18, 2009, w/Concise Explanation of the Relevance, three pages.
Korean Decision of Refusal Action dated Aug. 30, 2016 for patent application No. 10-2015-7033310 filed on Mar. 8, 2012, seven pages.
Korean Notice of Allowance dated Jan. 2, 2017 for Korean Application No. 10-2015-7033310, filed on Nov. 20, 2015, three pages.
Korean Office Action dated Aug. 20, 2015 for patent application No. 20137026479 filed on Mar. 8, 2012, three pages.
Korean Office Action dated Dec. 8, 2015 for patent application No. 20157033310 filed on Mar. 8, 2012, seven pages.
Russian Office Action—Decision to Grant dated Aug. 19, 2016 for Russian Patent Application No. 2013144845/07, filed on Mar. 8, 2012, thirteen pages.
U.S. Final Office Action dated Apr. 24, 2015 for U.S. Appl. No. 12/933,512, filed Nov. 24, 2010, nineteen pages.
U.S. Final Office Action dated Feb. 27, 2017 for U.S. Appl. No. 15/247,419, filed Aug. 25, 2016, ten pages.
U.S. Final Office Action dated Jul. 23, 2008, for U.S. Appl. No. 11/122,267, filed May 4, 2016, six pages.
U.S. Final Office Action dated Jun. 18, 2015, for U.S. Appl. No. 14/154,177, filed Jan. 13, 2014, eight pages.
U.S. Final Office Action dated Jun. 5, 2014, for U.S. Appl. No. 12/761,462, filed Apr. 16, 2010, fourteen pages.
U.S. Final Office Action dated Mar. 22, 2016 for U.S. Appl. No. 14/873,842, filed Oct. 2, 2015, eighteen pages.
U.S. Final Office Action dated May 11, 2011, for U.S. Appl. No. 11/412,715, filed Apr. 26, 2006, eight pages.
U.S. Final Office Action dated May 21, 2012, for U.S. Appl. No. 11/964,330, filed Dec. 26, 2007, twelve pages.
U.S. Final Office Action dated Nov. 24, 2009, for U.S. Appl. No. 11/009,965, filed Dec. 10, 2004, fourteen pages.
U.S. Non Final Office Action dated Apr. 2, 2009, for U.S. Appl. No. 11/009,965, filed Dec. 10, 2004, thirteen pages.
U.S. Non Final Office Action dated Aug. 16, 2013, for U.S. Appl. No. 12/761,462, filed Apr. 16, 2010, ten pages.
U.S. Non Final Office Action dated Aug. 16, 2013, for U.S. Appl. No. 12/761,523, filed Apr. 16, 2010, nine pages.
U.S. Non Final Office Action dated Dec. 10, 2010, for U.S. Appl. No. 11/412,715, filed Apr. 26, 2006, ten pages.
U.S. Non Final Office Action dated Dec. 14, 2011, for U.S. Appl. No. 11/412,715, filed Apr. 26, 2006, eight pages.
U.S. Non Final Office Action dated Feb. 1, 2017, for U.S. Appl. No. 14/860,687, filed Sep. 21, 2015, sixteen pages.
U.S. Non Final Office Action dated Feb. 3, 2010, for U.S. Appl. No. 11/626,308, filed Jan. 23, 2007, eleven pages.
U.S. Non Final Office Action dated Jan. 2, 2008, for U.S. Appl. No. 11/122,267, filed May 4, 2005, five pages.
U.S. Non Final Office Action dated Jan. 20, 2016, for U.S. Appl. No. 14/629,473, filed Feb. 23, 2015, fifteen pages.
U.S. Non Final Office Action dated Jan. 27, 2017, for U.S. Appl. No. 15/343,038, filed Nov. 3, 2016, fourteen pages.
U.S. Non Final Office Action dated Jul. 17, 2003, for U.S. Appl. No. 09/905,642, filed Jul. 13, 2001, six pages.
U.S. Non Final Office Action dated Jul. 2, 2013 for U.S. Appl. No. 12/933,512, filed Nov. 24, 2010, twelve pages.
U.S. Non Final Office Action dated Jun. 1, 2007, for U.S. Appl. No. 10/899,648, filed Jul. 26, 2004, seven pages.
U.S. Non Final Office Action dated Jun. 20, 2008, for U.S. Appl. No. 11/009,398, filed Dec. 10, 2004, fifteen pages.
U.S. Non Final Office Action dated Jun. 23, 2010, for U.S. Appl. No. 11/009,965, filed Dec. 10, 2004, fifteen pages.
U.S. Non Final Office Action dated Jun. 27, 2014 for U.S. Appl. No. 13/415,561, filed Mar. 3, 2012, fourteen pages.
U.S. Non Final Office Action dated Jun. 9, 2011, for U.S. Appl. No. 11/830,323, filed Jul. 30, 2007, five pages.
U.S. Non Final Office Action dated May 18, 2004, for U.S. Appl. No. 10/050,601, filed Jan. 15, 2002, eight pages.
U.S. Non Final Office Action dated Nov. 23, 2009, for U.S. Appl. No. 11/969,974, filed Jan. 7, 2008, seven pages.
U.S. Non Final Office Action dated Nov. 5, 2014, for U.S. Appl. No. 13/930,225, filed Jun. 28, 2013, six pages.
U.S. Non Final Office Action dated Oct. 23, 2013 for U.S. Appl. No. 13/415,561, filed Mar. 8, 2012, ten pages.
U.S. Non Final Office Action dated Oct. 5, 2016 for U.S. Appl. No. 15/247,419, filed Aug. 25, 2016, eight pages.
U.S. Non Final Office Action dated Oct. 7, 2011, for U.S. Appl. No. 11/964,330, filed Dec. 26, 2007; ten pages.
U.S. Non Final Office Action dated Sep. 12, 2014, for U.S. Appl. No. 14/154,177, filed Jan. 13, 2014, four pages.
U.S. Non Final Office Action dated Sep. 6, 2016 for U.S. Appl. No. 14/873,842, filed Oct. 2, 2015, seven pages.
U.S. Non Final Office Action with Restriction Requirement dated Mar. 4, 2011, for U.S. Appl. No. 11/830,323, filed Jul. 30, 2007, nine pages.
U.S. Appl. No. 15/416,876, filed Jan. 26, 2017 titled "Configurable Platform."
U.S. Appl. No. 15/584,405 titled "Imaging System for Combine Full-Color Reflectance and Near-Infrared Imaging," filed May 2, 2017.
U.S. Appl. No. 29/562,795, filed Apr. 28, 2016, titled "Device for Illumination and Imaging of a Target."
U.S. Notice of Allowance dated Dec. 30, 2016, for U.S. Appl. No. 14/873,842, filed Oct. 2, 2015, eleven pages.
U.S. Notice of Allowance dated Apr. 7, 2004, for U.S. Appl. No. 09/905,642, filed Jul. 13, 2001, six pages.
U.S. Notice of Allowance dated Aug. 26, 2004, for U.S. Appl. No. 10/050,601, filed Jan. 15, 2002, eight pages.
U.S. Notice of Allowance dated Aug. 6, 2015, for U.S. Appl. No. 13/853,656, filed Mar. 29, 2013, seven pages.
U.S. Notice of Allowance dated Dec. 10, 2012, for U.S. Appl. No. 11/964,330, filed Dec. 26, 2007, seven pages.
U.S. Notice of Allowance dated Feb. 25, 2010, for U.S. Appl. No. 11/969,974, filed Jan. 7, 2008, four pages.
U.S. Notice of Allowance dated Jan. 2, 2008, for U.S. Appl. No. 10/899,648, filed Jul. 26, 2004, three pages.
U.S. Notice of Allowance dated Jun. 25, 2015, for U.S. Appl. No. 12/933,512, filed Nov. 24, 2010 fourteen pages.
U.S. Notice of Allowance dated Mar. 22, 2013, for U.S. Appl. No. 11/964,330, filed Dec. 26, 2007, eight pages.
U.S. Notice of Allowance dated Mar. 28, 2016, for U.S. Appl. No. 13/853,656, filed Mar. 29, 2013, eight pages.
U.S. Notice of Allowance dated May 18, 2015, for U.S. Appl. No. 13/930,225, filed Jun. 28, 2013, nine pages.
U.S. Notice of Allowance dated Nov. 23, 2015, for U.S. Appl. No. 13/853,656, filed Mar. 29, 2013, seven pages.
U.S. Notice of Allowance dated Oct. 10, 2014, for U.S. Appl. No. 12/761,462, Apr. 16, 2010, ten pages.
U.S. Notice of Allowance dated Oct. 5, 2007, for U.S. Appl. No. 10/899,648, filed Jul. 26, 2004, six pages.
U.S. Notice of Allowance dated Sep. 10, 2013, for U.S. Appl. No. 11/412,715, filed Apr. 26, 2006, eight pages.
U.S. Notice of Allowance dated Sep. 14, 2012, for U.S. Appl. No. 11/830,323, filed Jul. 30, 2007, eight pages.
U.S. Supplemental Notice of Allowability dated Mar. 10, 2005, for U.S. Appl. No. 10/050,601, filed Jan. 15, 2002, five pages.
Written Opinion of the International Searching Authority dated Aug. 3, 2006, for International Application No. PCT/CA2006/000669, filed on Apr. 27, 2006, eight pages.
Written Opinion of the International Searching Authority dated Dec. 7, 2007, for International Application No. PCT/CA2007/001335, filed on Jul. 30, 2007, four pages.
Hubel, P.M. et al. (2004). "Spatial Frequency Response of Color Image Sensors: Bayer Color Filters and Foveon X3," *Proceedings of SPIE* 5301:402-406.
Australian Examination Report No. 1 dated Jun. 28, 2018 for Australian Application No. 2016351730 filed on Nov. 10, 2016, five pages.
Chinese First Office Action dated Sep. 26, 2018 for Chinese Patent Application No. 2018092001857100, filed on Sep. 4, 2017, nineteen pages.

(56) References Cited

OTHER PUBLICATIONS

European Decision to Grant dated Jul. 12, 2018 for EP Application No. 12754208.2 filed Oct. 4, 2013, two pages.
European Decision to Grant dated May 25, 2018 for EP Patent Application No. 13180297.7 filed Aug. 13, 2013, two pages.
European Notice of Allowance dated Feb. 28, 2018 for EP Patent Application No. 12754208.2 filed Oct. 4, 2013, six pages.
European Notice of Allowance dated Mar. 6, 2018 for EP Patent Application No. 13180297.7 filed Aug. 13, 2013, seven pages.
Indian Office Action dated Jan. 31, 2018 for Indian Patent Application No. 6532/DELNP/2010 filed on Sep. 16, 2010, five pages.
Indian Office Action dated Jun. 26, 2018 for Indian Patent Application No. 8678/DELNP/2013 filed on Mar. 8, 2012, five pages.
International Preliminary Report on Patentability dated May 24, 2018 for International Application No. PCT/CA2016/051315 filed on Nov. 10, 2016, nine pages.
Japanese Notice of Allowance dated Apr. 2, 2018 for Japanese Patent Application No. 2017-018858 filed on Feb. 3, 2017, six pages.
Japanese Office Action dated Dec. 8, 2017 for Japanese Patent Application No. 2017-018858 filed on Feb. 3, 2017, six pages.
U.S. Final Office Action dated Feb. 1, 2018, for U.S. Appl. No. 15/584,405, filed May 2, 2017, ten pages.
U.S. Non Final Office Action dated Aug. 15, 2018 for U.S. Appl. No. 15/348,664, filed Nov. 10, 2016, eleven pages.
U.S. Non Final Office Action dated Jun. 5, 2018, for U.S. Appl. No. 14/860,687, filed Sep. 21, 2015, eighteen pages.
U.S. Non Final Office Action dated Jun. 8, 2018, for U.S. Appl. No. 15/584,405, filed May 2, 2017, eight pages.
U.S. Non Final Office Action dated May 25, 2018, for U.S. Appl. No. 15/343,038, filed Nov. 3, 2016, eleven pages.
U.S. Appl. No. 15/810,911, filed Nov. 13, 2017. (Copy not submitted herewith pursuant to the waiver of 37 C.F.R. § 1.98(a)(2)(iii) issued by the Office dated Sep. 21, 2004.).
Australian Office Action dated May 10, 2019 for Australian Patent Application No. 2016351730 filed on Nov. 10, 2016, ten pages.
Canadian Office Action dated Feb. 19, 2019 for CA Patent Application No. 2,998,920 filed on Mar. 16, 2018, four pages.
European Notice of Allowance dated Mar. 18, 2019 for EP Patent Application No. 09819758.5, filed on May 4, 2011, seven pages.
European Search Report dated Feb. 18, 2019 for EP Patent Application No. 18178620.3 filed on Jun. 19, 2018, eight pages.
International Preliminary Report on Patentability dated Dec. 27, 2018 for International Patent Application No. PCT/CA2017/050734 filed on Jun. 14, 2017, six pages.
U.S. Final Office Action dated Dec. 14, 2018 for U.S. Appl. No. 15/584,405, filed May 2, 2017, seven pages.
U.S. Final Office Action dated Jan. 11, 2019 for U.S. Appl. No. 15/343,038, filed Nov. 3, 2016, twelve pages.
U.S. Final Office Action dated Jan. 14, 2019 for U.S. Appl. No. 14/860,687, filed Sep. 21, 2015, sixteen pages.
U.S. Non Final Office Action dated Apr. 3, 2019 for U.S. Appl. No. 15/416,876, filed Jan. 26, 2017, thirteen pages.
U.S. Non Final Office Action dated Feb. 5, 2019 for U.S. Appl. No. 15/623,100, filed Jun. 14, 2017, ten pages.
U.S. Appl. No. 16/441,493, filed Jun. 14, 2019. (Copy not submitted herewith pursuant to the waiver of 37 C.F.R. § 1.98(a)(2)(iii) issued by the Office dated Sep. 21, 2004).
U.S. Restriction Requirement dated Feb. 7, 2019 for U.S. Appl. No. 29/562,795, filed Apr. 28, 2016, seven pages.
Australian Notice of Acceptance for Patent Application dated Jun. 26, 2019 for Patent Application No. 2016351730 filed on Nov. 10, 2016, three pages.
Brazilian Office Action dated Aug. 5, 2019, for Patent Application No. BR1120130229977, filed Mar. 8, 2012, 4 pages (including English Translation).
Canadian Office Action dated Nov. 5, 2019, for Canadian Patent Application No. 3027592, filed on Jun. 14, 2017, four pages.
European Extended Search Report dated May 7, 2019, for Patent Application No. 16863277.6, filed Nov. 10, 2016, 3 pages.
European Extended Search Report dated Oct. 16, 2019, for Patent Application No. 17743524.5, filed Jan. 26, 2017, 4 pages.
Japanese Office Action dated Jul. 12, 2019, for Patent Application No. 2018-516161, filed Nov. 10, 2016, 21 pages (including English translation).
Sensitivation (photography), definition from Wikipedia, original language German, 6 pages (Machine Translation).
U.S. Final Office Action dated Jul. 25, 2019 for U.S. Appl. No. 15/416,876, filed Jan. 26, 2017, 13 pages.
U.S. Non Final Office Action dated Aug. 2, 2019 for U.S. Appl. No. 15/623,100, filed Jun. 14, 2017, 12 pages.
U.S. Non Final Office Action dated Aug. 21, 2019 for U.S. Appl. No. 15/584,405, filed May 2, 2017, 6 pages.
U.S. Non-Final Office Action dated Aug. 23, 2019 for U.S. Appl. No. 15/343,038, filed Nov. 3, 2016, 14 pages.
U.S. Non-Final Office Action dated Aug. 23, 2019, for U.S. Appl. No. 14/860,687, filed Sep. 21, 2015, 14 pages.
U.S. Non-Final Office Action dated Sep. 27, 2019, for U.S. Appl. No. 29/562,795, filed Apr. 28, 2016, 6 pages.
Chinese Notice of Allowance dated Jan. 13, 2020, for Patent Application No. 201710785223.7, filed Mar. 8, 2012, six pages.
Japanese Office Action dated Jan. 10, 2020, for Japanese Patent Application No. 2018-516161, filed Nov. 10, 2016, five pages.
U.S. Non-Final Office Action dated Jan. 16, 2020, for U.S. Appl. No. 15/416,876, filed Jan. 26, 2017, 13 pages.

\* cited by examiner

|    | Cy | Ye | Cy | Ye |
|----|----|----|----|----|
|    | G  | Mg | G  | Mg |
|    | Cy | Ye | Cy | Ye |
|    | G  | Mg | G  | Mg |
|    | Cy | Ye | Cy | Ye |

B1 = rows 1–2, B2 = rows 3–4 (A1 = rows 1–2, A2 = rows 3–4)

FIG. 5A

First field readout values

| A1 | G+Cy  | Mg+Ye | G+Cy  | Mg+Ye |
|----|-------|-------|-------|-------|
| A2 | Mg+Cy | G+Ye  | Mg+Cy | G+Ye  |

FIG. 5B

Second field readout values

| B1 | G+Cy  | Mg+Ye | G+Cy  | Mg+Ye |
|----|-------|-------|-------|-------|
| B2 | Mg+Cy | G+Ye  | Mg+Cy | G+Ye  |

FIG. 5C

|     |     |     |     |
| --- | --- | --- | --- |
| Cy  | Ye  | Cy  | Ye  |
| G   | Mg  | G   | Mg  |
| Cy  | Ye  | Cy  | Ye  |
| G   | Mg  | G   | Mg  |
| Cy  | Ye  | Cy  | Ye  |

B1, B2 (row labels); A1, A2, A3 (row indicators)

FIG. 6A

First field readout values

| A1 | Cy | Ye | Cy | Ye |
| --- | --- | --- | --- | --- |
| A2 | Cy | Ye | Cy | Ye |

FIG. 6B

Second field readout values

| B1 | G  | Mg | G  | Mg |
| --- | --- | --- | --- | --- |
| B2 | Mg | G  | Mg | G  |

FIG. 6C

Timing Diagram Details

| Time | Full CCD illumination for interval from $T_i$ to $T_{i+1}$ | CCD Lines | CCD signal read out | Signal ID | Display signal written to buffer | Color image | Fluorescent image |
|---|---|---|---|---|---|---|---|
| T1 | Fluorescence + Full color | Even | Fluorescence only | F1 | (FL6 = F6 + F1) | | (FL6) |
| T2 | Fluorescence only | Odd | Fluorescence + Full color | C1 | (CL12 = C12 + C1) | (CL12 ~ FL6) | |
| T3 | Fluorescence only | Even | Fluorescence + Full color | C2 | CL1 = C1 + C2 | (CL1 ~ FL6) | FL1 |
| T4 | Fluorescence + Full color | Odd | Fluorescence only | F2 | FL1 = F1 + F2 | CL2 ~ FL1 | |
| T5 | Fluorescence only | Even | Fluorescence + Full color | C3 | CL2 = C1 + C3 | CL3 ~ FL1 | FL2 |
| T6 | Fluorescence only | Odd | Fluorescence + Full color | C4 | CL3 = C3 + C4 | CL4 ~ FL2 | |
| T7 | Fluorescence + Full color | Even | Fluorescence only | F3 | FL2 = F2 + F3 | CL5 ~ FL2 | |
| T8 | Fluorescence only | Odd | Fluorescence + Full color | C5 | CL4 = C3 + C5 | CL6 ~ FL3 | FL3 |
| T9 | Fluorescence only | Even | Fluorescence + Full color | C6 | CL5 = C5 + C6 | CL7 ~ FL3 | |
| T10 | Fluorescence + Full color | Odd | Fluorescence only | F4 | FL3 = F3 + F4 | CL8 ~ FL4 | FL4 |
| T11 | Fluorescence only | Even | Fluorescence + Full color | C7 | CL6 = C5 + C7 | CL9 ~ FL4 | |
| T12 | Fluorescence only | Odd | Fluorescence + Full color | C8 | CL7 = C7 + C8 | CL10 ~ FL5 | |
| T13 | Fluorescence + Full color | Even | Fluorescence only | F5 | CL8 = C7 + C9 | CL11 ~ FL5 | FL5 |
| T14 | Fluorescence only | Odd | Fluorescence + Full color | C9 | CL9 = C9 + C10 | CL12 ~ FL6 | |
| T15 | Fluorescence only | Even | Fluorescence + Full color | C10 | FL4 = F4 + F5 | CL10 ~ FL5 | |
| T16 | Fluorescence + Full color | Odd | Fluorescence only | F6 | FL5 = F5 + F6 | CL11 ~ FL5 | FL6 |
| T17 | Fluorescence only | Even | Fluorescence + Full color | C11 | CL10 = C9 + C11 | CL12 ~ FL6 | |
| T18 | Fluorescence only | Odd | Fluorescence + Full color | C12 | CL11 = C11 + C12 | CL11 ~ FL5 | |
| T1 | Fluorescence + Full color | Even | Fluorescence only | F1 | FL6 = F6 + F1 | CL12 ~ FL6 | FL6 |
| T2 | Fluorescence only | Odd | Fluorescence + Full color | C1 | CL12 = C12 + C1 | CL12 ~ FL6 | |
| T3 | Fluorescence only | Even | Fluorescence + Full color | C2 | CL1 = C1 + C2 | CL1 ~ FL6 | |

FIG. 8

IMAGING SYSTEMS AND METHODS FOR DISPLAYING FLUORESCENCE AND VISIBLE IMAGES

RELATED APPLICATIONS

This application is a continuation of U.S. application Ser. No. 14/860,687, filed Sep. 21, 2015, which is a continuation of U.S. application Ser. No. 13/930,225, filed Jun. 28, 2013, now U.S. Pat. No. 9,143,746, which is a continuation of U.S. application Ser. No. 11/964,330, filed Dec. 26, 2007, now U.S. Pat. No. 8,498,695, which claims the benefit of U.S. Provisional Application No. 60/908,373, filed Mar. 27, 2007, and U.S. Provisional Application No. 60/876,597, filed Dec. 22, 2006, the disclosures of all of which are incorporated herein by reference as if fully set forth herein.

BACKGROUND OF THE INVENTION

The invention is directed to methods and systems for simultaneous real-time fluorescence and color video endoscopy at close to video frame rates. The invention is also directed to high-efficiency illumination sources and to methods and systems for controlling temporal and spectral output of these light sources.

Medical endoscopy is increasingly employing specialized optical imaging techniques, such as fluorescence (i.e. autofluorescence and photodynamic) endoscopy, narrow band imaging and other techniques, for improved visualization and for the detection and diagnosis of diseases, Endoscopic imaging systems that provide specialized imaging modes typically also operate in a conventional color, or white-light, endoscopy mode. Embodiments of endoscopic imaging systems incorporating both a color and fluorescence imaging modes have been disclosed, for example, in U.S. Pat. No. 6,462,770 B1, U.S. Pat. No. 6,821,245 B1, and U.S. Pat. No. 6,899,675 B2.

In conventional white-light endoscopy, hereinafter also referred to as color imaging mode, light in the visible spectral range is used to illuminate the tissue surface under observation. Light reflected by the tissue passes through a suitable lens system and is incident on an image sensor built into or attached to the endoscope. The electrical signals from the image sensor are processed into a full color video image which can be displayed on a video monitor or stored in a memory. In fluorescence endoscopy, fluorescence excitation light excites fluorophors in the tissue, which emit fluorescence light at an emission wavelength which is typically greater than the excitation wavelength. Fluorescence light from the tissue passes through a suitable lens system and is incident on the image sensor. The electrical signals from the image sensor are processed into a fluorescence video image which can be displayed on a video monitor, either separately from or together with the color video image, or stored in a memory.

The fluorescence excitation and emission wave-lengths depend upon the type of fluorophors being excited. In the case of exogenously applied fluorophors, the band of excitation wavelengths may be located anywhere in the range from the ultraviolet (UV) to the near infra-red (NIR) and the emission wavelength band anywhere from the visible to the NIR. For fluorophors endogenous to tissue, the band of excitation and emission wavelengths are more limited (excitation from the UV to the green part of the visible spectrum, emission from the blue-green to the NIR).

In a conventional fluorescence/white-light endoscopic imaging system, the system can be switched between color and fluorescence modes either automatically or with a hand- or foot-operated external switch. Both the illumination and imaging characteristics of the endoscopic imaging system may require adjustment when switching the operation of an endoscopic imaging system from one mode to the other. For example, gain adjustments and additional image processing (e.g., pixel binning, time averaging, etc.) may be required because the image signal in color imaging mode tends to be substantially greater than the image signal from endogenous (tissue) fluorescence. Although switching between imaging modes with an automated device is not difficult, additional time may be required to complete the endoscopic procedure because areas of interest are examined sequentially in each mode.

It would therefore be desirable to provide an endoscopic imaging system capable of acquiring and displaying images in both conventional color ("white-light") and fluorescence imaging modes simultaneously. It would further be desirable to employ high-efficiency illumination sources that can be easily controlled over the spectral range of interest for endoscopy.

SUMMARY OF THE INVENTION

The invention disclosed herein describes an endoscopic video system and method using a single color image sensor for fluorescence and color imaging and for simultaneously displaying the images acquired in these imaging modes at video rates. The color imager may include a CCD color image sensor. The endoscopic video system has no moving parts.

According to one aspect of the invention, tissue is illuminated continuously with fluorescence excitation light and is further illuminated periodically using visible light outside of the fluorescence excitation wavelength range. The method furthermore utilizes an excitation light blocking filter which substantially blocks the excitation light while allowing the blue, green and red components of the illumination light to pass to the color image sensor. In one embodiment, the single color image sensor may be disposed in the tip of the endoscope, in which case the excitation light blocking filter is mounted in or on the tip of video endoscope.

With the method of the invention, fluorescence images are acquired during a time period when only the excitation light is supplied as illumination, while color images are acquired during a time period when the combination of both excitation light and visible light outside of the excitation wavelength range are supplied as illumination. The image fields are read out from the single CCD color image sensor in an interlaced fashion and processed to produce corresponding full-frame fluorescence and white-light images. Real-time fluorescence and white-light images of the tissue are then produced by subtracting from each full-frame combined fluorescence and white-light image the corresponding fluorescence image on a pixel-by pixel basis.

In one embodiment, the illumination light may be switched on for one cycle and switched off for two cycles, wherein a different image field of the combined tissue fluorescence and white-light image is read out during each of the two cycles when the illumination light is switched off, and a different image field of the tissue fluorescence image are read out during each of the cycles when the illumination light is switched on. A cycle may have a duration of $\frac{1}{60}$ second. Four full frame white-light images and two full frame fluorescence images may be generated every six cycles.

The image data can be interpolated during cycles when no actual image data are available. For example, during a cycle where no full frame white-light image is produced, an interpolated full frame white-light image may be computed from two adjacent full frame white-light images. Likewise, the fluorescence signals may be interpolated between sequential fluorescence frames before being subtracted from the white-light image signals.

In yet another embodiment, pixel values of adjacent rows of the CCD color image sensor are added pixel-by-pixel to form summed row pixel values and the summed values are read out in an interlaced fashion.

In one embodiment, a high-resolution video image may be generated by computing a luma image of the combined full-frame fluorescence and white-light image signals and colorizing the luma image based on a ratio of red reflectance to fluorescence signals to produce a superimposed fluorescence/color image for display. Processing an image based on the luma data enhanced the attainable spatial resolution. A change in tissue pathology, as indicated by a change in the fluorescence signal from that tissue, can be represented as a change in color in the video image.

Further features and advantages of the present invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIGS. 5A-5C show a filter arrangement on a CMGY image sensor (FIG. 5A) and interlaced readout (FIGS. 5B-5C) with summing on chip;

FIGS. 6A-6C show a filter arrangement on a CMGY image sensor (FIG. 6A) and interlaced readout (FIGS. 6B-6C) without summing on chip;

FIG. 8 shows a timing diagram for reading from the color sensor fluorescence and color image information;

DETAILED DESCRIPTION OF THE INVENTION

In conventional white-light (color imaging) endoscopy, broadband visible light is used to illuminate the tissue under observation. Historically, endoscopes used for white light endoscopy have incorporated fiberoptic light guides to transmit light from lamps to provide this type of illumination. In fluorescence endoscopy, fluorophors in the tissue are excited by illumination with a shorter wavelength light and the resulting fluorescence emission is detected at Stokes-shifted longer wavelengths. The fluorophors may be either endogenous to the tissue (i.e., naturally present) or exogenous (e.g., dyes applied to enhance contrast for diagnostic or other imaging purposes). Since the fluorescence process tends to be rather inefficient, the intensity of the shorter wavelength excitation light is typically several orders of magnitude greater than the intensity of the resulting fluorescence emission. As such, both direct visualization and imaging of emissions from fluorophors requires the use of a barrier filter that blocks transmission of the reflected shorter wavelength excitation light and prevents the excitation light from overwhelming the eye or image sensor used to observe/detect the emitted fluorescence. A certain minimum level of excitation light intensity is also required to provide the desired quality of (optical or electronic) image signal. The desired amount of excitation light will depend on the type and concentration of fluorophors to be excited, distance to the tissue and size of the area being visualized imaged, the sensitivity of the eye/image sensor and similar related factors. As a result, particularly in the case of natural (i.e., endogenous) tissue fluorescence, endoscopy imaging systems operating in fluorescence mode typically employ powerful arc lamps or lasers to excite fluorophors as well as highly sensitive cameras to image fluorescence emissions from these fluorophors.

Figure 1:
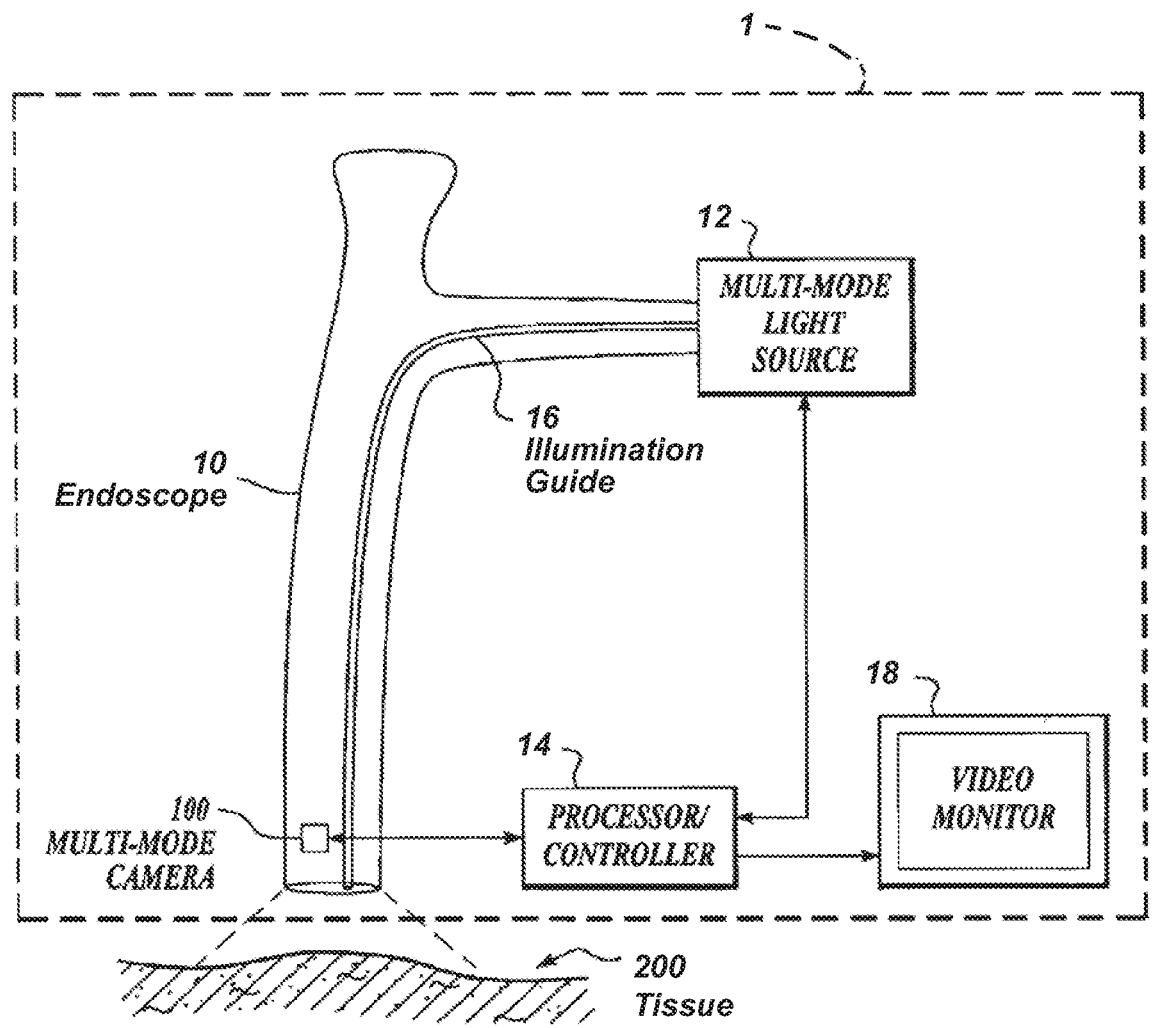
FIG. 1 shows a schematic block diagram of an exemplary fluorescence endoscopy video system with a single distal color image sensor.

FIG. 1 is a block diagram of a fluorescence endoscopy video system 1 in accordance with one embodiment of the present invention. The system includes a multi-mode light source 12 that generates light for obtaining color and fluorescence images. The use of the light source for obtaining different kinds of images will be described in further detail below. Light from the light source 12 is supplied to an illumination guide 16 of an endoscope 10, which then illuminates a tissue sample 200 that is to be imaged.

As also shown in FIG. 1, the system also includes a camera 100, for example, a solid-state camera based on a CCD or CMOS sensor chip, which in the exemplary embodiment is located at the distal or insertion end of the endoscope 60. Alternatively, although not illustrated, the camera 100 may also be positioned at another location, such as the proximal end of the endoscope 60. In the depicted embodiment, the light from the tissue is directly captured by the camera 100, and the operation of the system is similar to video endoscopes currently on the market (such as the Olympus CF-240L).

A processor/controller 14 controls the camera 100 and the light source 12, which will be described in more detail below, and produces video signals that are displayed on a video monitor 18. The processor/controller 14 communicates with the camera 100 by wire or other signal communication devices that are routed within the endoscope, such as optical fiber. Alternatively, communication between the processor/controller 14 and the camera 100 can be conducted over a wireless link. Clinically relevant information about the health of the tissue under observation may be contained in the intensity of the fluorescence emission within a specific wavelength range.

For autofluorescence endoscopy (endoscopy using endogenous fluorophors), such information is contained in the green wavelength range of the emitted fluorescence. It has been observed that green florescence is increasingly suppressed as the tissue becomes increasingly diseased. However, the red fluorescence signal does not vary with the disease state of the tissue and can hence be used to distinguish between intensity variation in the green fluorescence emission due to the disease state of the tissue and intensity variations due to imaging artifacts, such as shadows or geometry effects (e.g., imaging distance). A single multicolor image can be formed in which the color is indicative of the health of the examined tissue by combining the image information from a wavelength range that varies with the disease state (green fluorescence) with the image information from a wavelength range that does not vary with the disease state (red fluorescence) of the tissue.

Figure 2:
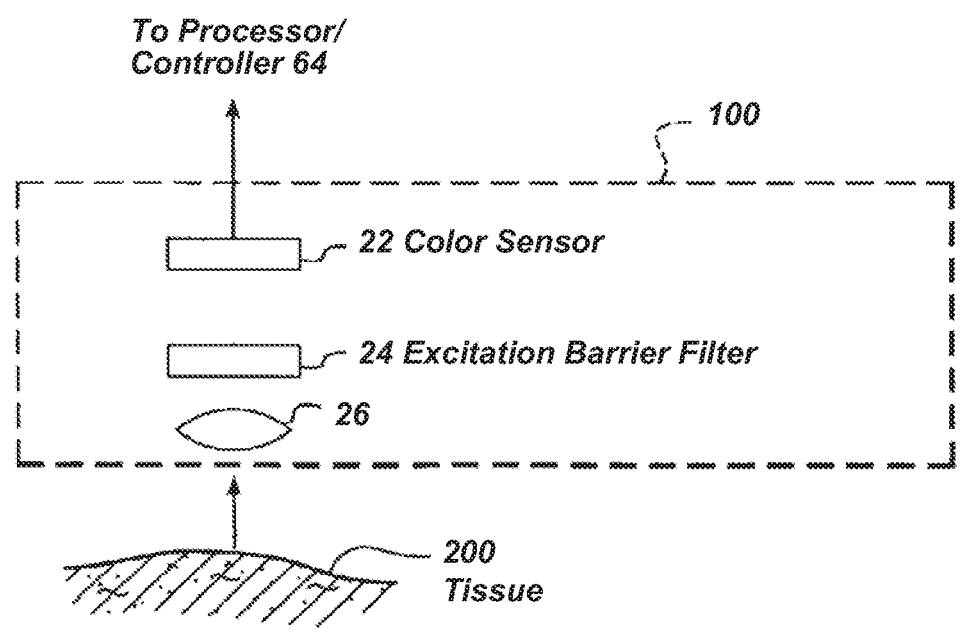
FIG. 2 shows the camera of FIG. 1 with an excitation light blocking filter.

FIG. 2 shows schematically an exemplary embodiment of camera 100 with color image sensor 22 and light collimating optics 26. Positioned between the tissue 200 and color image sensor 22 is an excitation light blocking filter 24 which blocks reflected excitation light from reaching image sensor 22, while allowing imaging light and fluorescence light to pass. The advantage of this configuration is that all imaging is performed and controlled by the same imaging optics 113. In an alternative embodiment, the excitation light blocking filter 24 may be placed distal of the light collimating optics 26, and in some embodiments may be disposed on the outside of the distal tip of the endoscope, for example, when converting a white-light imaging endoscope into an imaging/fluorescence endoscope. An externally mounted excitation light blocking filter is described in, for example, commonly assigned U.S. application Ser. No. 11/412,715.

The white light/fluorescence video endoscopy system of the invention operates by illuminating the sample with either excitation light alone or with a combination of excitation light and illumination light in a wavelength range or in wavelength ranges outside the spectral range of the excitation spectrum. The light source for excitation light and illumination light can be, for example, an arc lamp, a solid state light emitter such as one or more diode lasers or light emitting diodes, or any other light source emitting light in a suitable wavelength range. The light source can be a single light source, wherein a portion of the light is filtered out to provide excitation light, and another portion of the light is filtered out to provide illumination light. Alternatively, different light sources can be provided for excitation light and illumination light, respectively. The illumination light is timed, either by using an external shutter 37 or, if light sources with a rapid response are used, by turning the light sources on and off.

Figure 3:
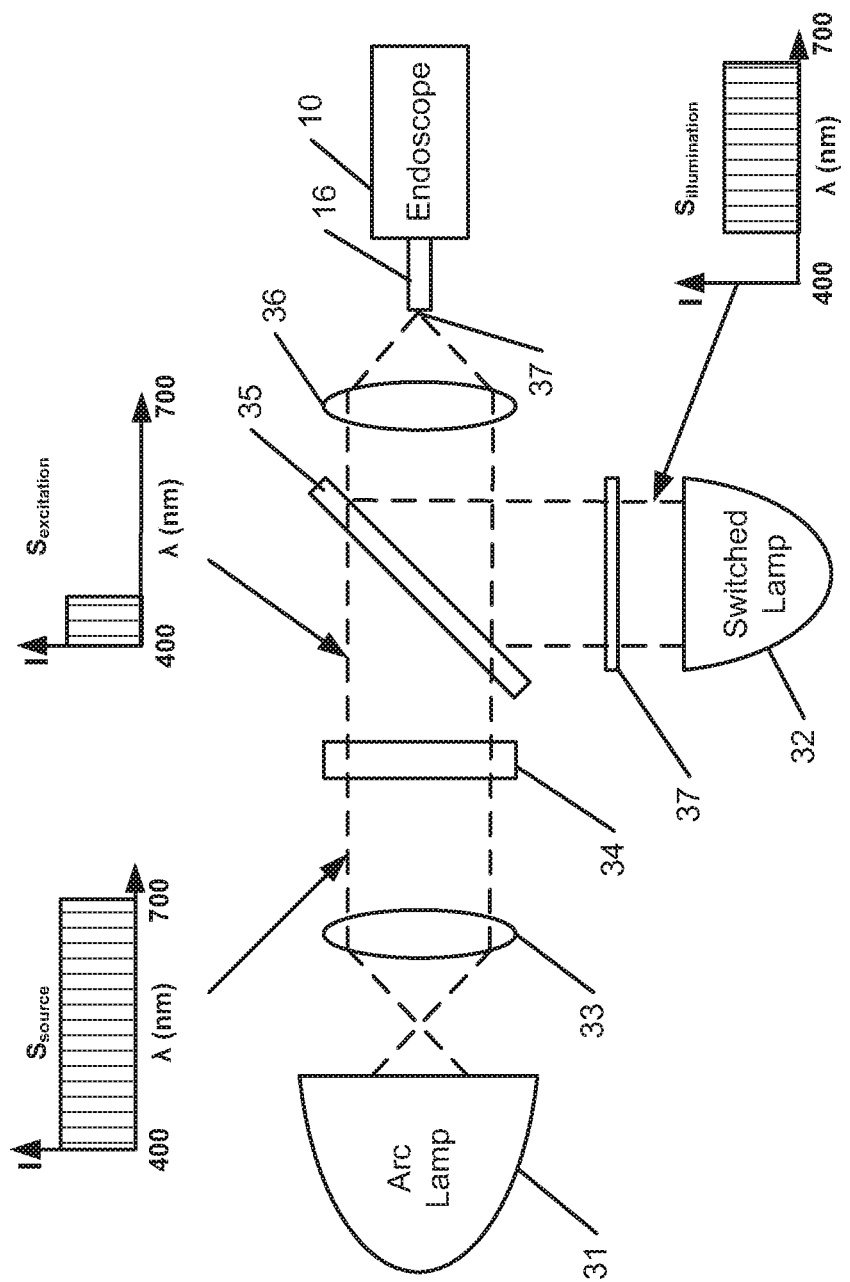
FIG. 3 shows a schematic block diagram of a first exemplary embodiment of an illumination source according to the invention.

FIG. 3 shows in more detail a first embodiment of a multi-mode light source 30 for simultaneously illuminating a tissue sample 200 with continuous fluorescence excitation light and switched illumination light. Light source 30 includes a first light source 31, for example, an arc lamp, and a collimating lens 33 for producing a high intensity, preferably collimated spectral output $S_{source}$ which includes an excitation wavelength range. A bandpass filter 34 filters out spectral components outside the excitation wavelength range $S_{excitation}$ and allows only spectral components within the excitation wavelength range $S_{excitation}$ to pass. Light source 30 further includes a second light source 32, for example, a halogen lamp, for producing a preferably collimated spectral output $S_{illumination}$ with a high intensity in an imaging wavelength range covering, for example, the visible spectral range. Light source 32 may be switched with timing signals produced by processor/controller 14, for example, by placing a mechanical or electronic shutter 37 between second light source 32 and dichroic mirror 3S or by controlling the electric current supplied to light source 32. The combined collimated excitation/imaging light is focused by lens 36 onto the input face 37 of an optical fiber illumination guide 16 with a suitable numerical aperture (NA).

Figure 4:
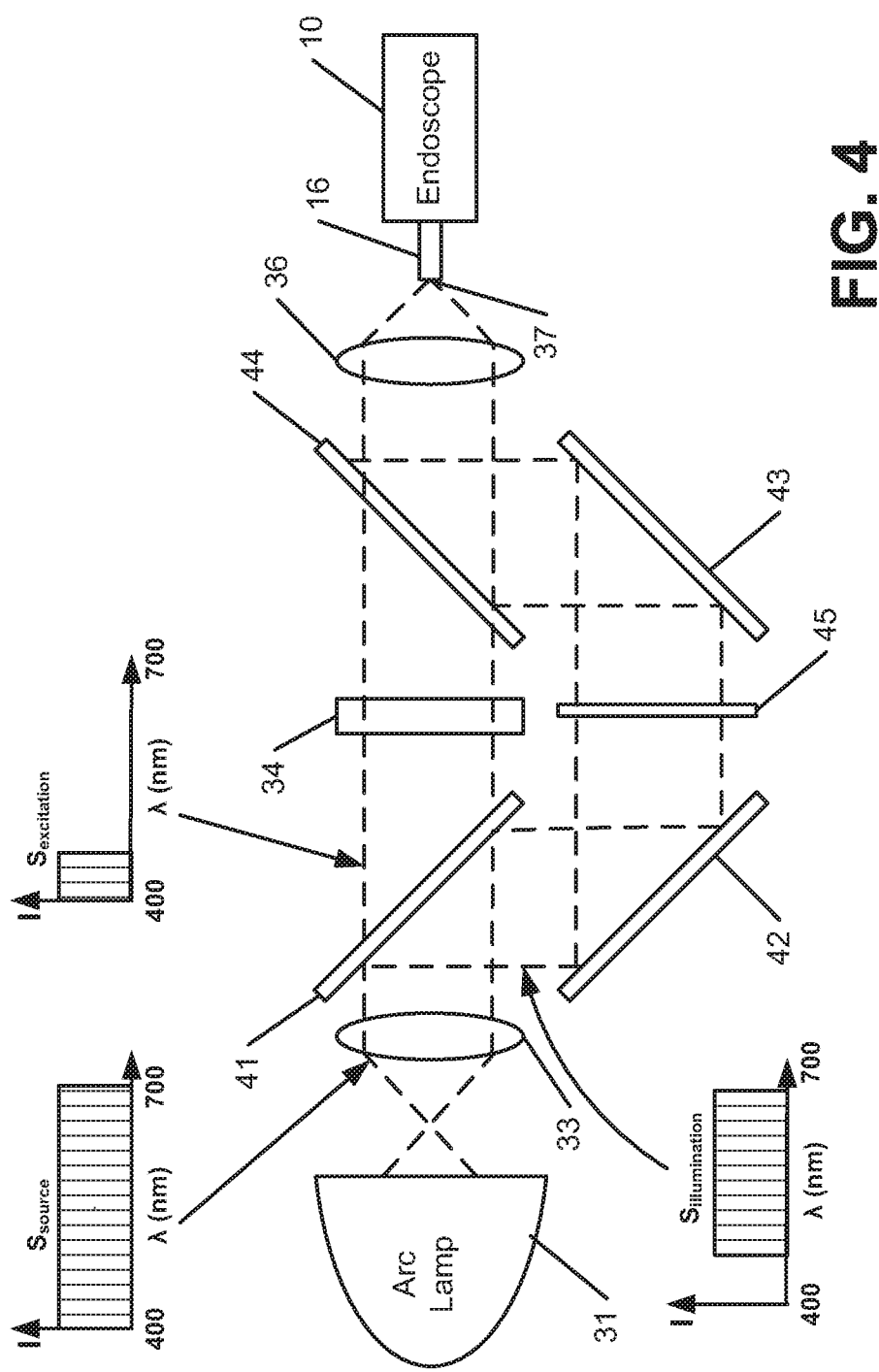
FIG. 4 shows a schematic block diagram of a second exemplary embodiment of an illumination source according to the invention.

FIG. 4 shows a second embodiment of a multi-mode light source 40 for simultaneously illuminating a tissue sample 200 with continuous fluorescence excitation light and switched illumination light. Light source 40 includes an excitation/illumination light source 31, for example, an arc lamp, and a collimating lens 33 for producing a high intensity, preferably collimated spectral output $S_{source}$ which includes an excitation wavelength range $S_{excitation}$. A dichroic mirror 41 reflects the spectral illumination component $S_{illumination}$ and passes the excitation wavelength range $S_{excitation}$ which may be additionally narrow-band filtered by bandpass filter 34. The light component reflected off a first dichroic mirror 41 is then reflected by mirror 42, passes through a shutter 45 (mechanical or electronic) and is then further reflected by mirror 43 and reflected at second dichroic mirror 44 to become collinear with the excitation light passing through filter 34. As before, the combined collimated excitation/imaging light is focused by lens 36 onto the input face 37 of an optical fiber illumination guide 16 with a suitable numerical aperture (NA). This embodiment takes advantage of the fact that a suitable arc lamp can emit over a wavelength range which covers both the excitation light spectrum and the illumination light spectrum. The shutter 4S may be switched by timing signals produced by processor/controller 14.

Suitable filters, for example, a low-pass filter to block excitation light and/or a high-pass filter to block unswitched illumination light, may be placed along the optical paths.

In operation, when the switched light source 32 is off (or the shutter 4S is closed), only excitation light illuminates the tissue 200, for example, through the endoscope illumination guide 16. The reflected excitation light is blocked from reaching the color image sensor by the excitation light blocking filter 24, while tissue fluorescence light passes through the excitation light blocking filter 24 and reaches the color image sensor 22 for fluorescence light detection.

When the illumination light source 32 is switched on (or the shutter 45 is open), the combined light from the illumination light source 32 and the excitation light source 31 is coupled into the endoscope light guide 14 and illuminates the tissue 200. The reflected excitation light (and any residual light from the switched light source at that wavelength) is blocked as before by the excitation light blocking filter 24, while the combination of both tissue fluorescence and reflected illumination light ("white light") is imaged by the color image sensor 22.

FIGS. 5A-5C show an exemplary arrangement of spectral filter elements disposed on the pixels of a CMGY image sensor (FIG. 5A) and an interlaced readout (FIGS. 5B-5C) with on-chip summing of pixels from adjacent rows. The first half-frame in the embodiment depicted in FIGS. 5A, 5B, 5C is here composed of the sum of lines 1 and 2; 3 and 4; 5 and 6; and so on, whereas the second half-frame is composed of the sum of lines 2 and 3; 4 and 5; and so on. FIG. 6A shows the same filter arrangement as in FIG. 5A, but with a different interlaced readout (FIGS. 6B-6C) without on-chip summing. The first half-frame in the embodiment depicted in FIGS. 6A, 6B, 6C is composed of lines 1; 3; 5; and so on, whereas the second half-frame is composed of the lines 2; 4; and so on, Most video endoscopes and endoscopic video cameras currently use COD image sensors with CMGY color filters since these tend to provide the highest quality color images.

Figure 7:
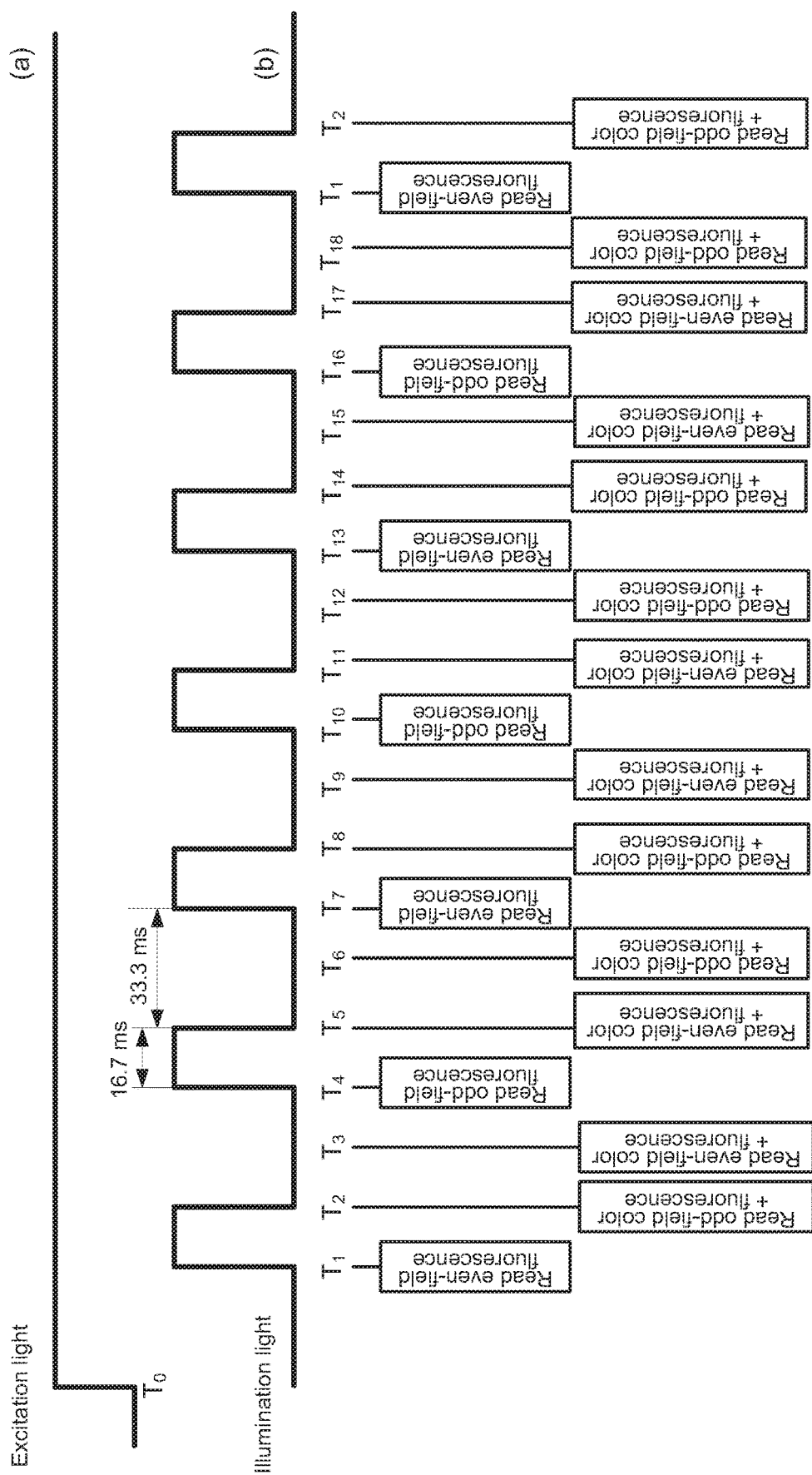
FIG. 7 shows a timing diagram for excitation light and imaging light exposure.

FIG. 7 shows a timing diagram according to the invention for operating the exemplary endoscope system. As can be seen from curve (a) in the diagram, the excitation light source 31 is turned on at time $T_0$, irradiating the tissue continuously with fluorescence excitation light. Conversely, as depicted by curve (b), the illumination light source 32 is periodically switched on and off (or shutter 37 or 45 is opened and closed) with a duty factor of 33%, i.e. the illumination light source is turned on at times $T_1$, $T_4$, $T_7$, ... (i.e., at times $T_{1+3*n}$ with n=0, 1, 2 ... ) for one field period and turned off again at times $T_2$, $T_5$, $T_8$, ..., $T_{2+3*n}$ for two field periods, which include times $T_3$, $T_6$, $T_9$, ..., $T_{3+3*n}$. In the depicted example, a field period has a duration of $\frac{1}{60}$ s=16.7 ms.

As mentioned above, the exemplary image sensor is read out in an interlaced fashion, so that even lines and odd lines are read alternatingly, with or without summation on the chip. An image with full vertical resolution is then generated in the video processor/controller 14 by combining two sequential interlaced fields to form a full video frame for the fluorescence image and for the combined fluorescence/white-light image.

FIG. 8 describes in more detail the temporal illumination and readout pattern of the interlaced CCD image as a function of time.

Before the image acquisition begins in the depicted example at time $T_1$, the COD is illuminated only with fluorescence excitation light. The even-fields acquired in the time interval preceding $T_1$ contain fluorescence-only data which are read out at $T_1$. At the same time, the illumination light is turned on, so that the COD is now illuminated with fluorescence excitation light and illumination light between the times $T_1$ and $T_2$.

The illumination light is turned off at time $T_2$, in the present example after 16.7 ms, and the image data representing "color-plus-fluorescence" are read out for the odd field at $T_2$ and for the even field at $T_3$. The COD is illuminated from $T_2$ until $T_4$ with fluorescence light only and acquires a new fluorescence signal. It should be noted that the fluorescence signal is acquired during two field periods, whereas the added illumination light is acquired only during one field period, which provides an improved signal over other methods, where the fluorescence signal and the illumination signal are acquired with the same duty cycle.

The image signals from the color image sensor acquired alternatingly during "fluorescence-only" and "color-plus-fluorescence" measurements are supplied to processor/controller 14 which stores and processes the image signals to form the desired images for display. The processor/controller 14 may be, for example, a processor selected from the Texas Instruments C64XX family of image processors. The processing of a specific field depends on whether the field is to be used to generate a fluorescence image or a color (white tight) image. The processor/controller 14 may also synchronize the operation of the switched illumination light source with the image acquisition, as described above.

This exposure and read-out scheme described above generates from the combination of odd and even fields a full frame of fluorescence image information every six field time periods. In the depicted example, each field time period is 16.7 ms. In other words, the full frame fluorescence image is completely updated every tenth of a second. During the same six (6) field periods, four fields (two even fields and two odd fields) of color image information are generated and these even-and odd-line fields are suitably combined and processed to generate four (4) full vertical resolution color video frames during the same six (6) field periods. As seen in column 6 of FIG. 8, the display signal written into buffer memory still includes the fluorescence signal component, which is then subtracted to yield the color image signal. The transformation of image data from the CMGY image space to the RGB image space for display is conventional and will not be described further.

Because during six (6) field periods the image data contain only 2 (two) fields of color information, rather than three (3) video frames, the image data may advantageously be interpolated between sequential data points. In this way, the image quality can be improved by providing a smooth transition between frames, so that the final color video image is perceived by the human eye as being substantially similar to the field update rate in a normal video signal.

Once the image signals in Column 6 of FIG. 8 are transferred to the image processor 14, the color (white-light) images and the fluorescence images are separated on a frame-by-frame basis. The color information is extracted from these frames (i.e. the contribution from the fluorescence signal is removed) by subtracting pixel-by-pixel a fluorescence signal value from each "color-plus-fluorescence" frame. Advantageously, the subtracted fluorescence signal values are interpolated from the preceding stored "fluorescence-only" frame and the "fluorescence-only" frame following the "color-plus-fluorescence" frame being processed. This causes at most a delay of two fields, in the present example of 66.7 ms, between image acquisition and display.

After the fluorescence contribution is subtracted, the color balance of the remaining image signals may still need to be corrected for proper white balance. This correction may be performed using conventional image processing and color-space transformation methods by using a compensation matrix or similar processing techniques, which convert the image signal from one color space to another. The processing of fluorescence image fields is somewhat less complex because the fluorescence image data do not include image data from other sources. Accordingly, fluorescence image data produced in multiple, non-overlapping spectral ranges may be processed and displayed as a real color or false color image (for example, green fluorescence from fluorescein) may be displayed as green and IR fluorescence from ICG may be displayed as red, etc., in the same fashion as white light color images are processed and displayed on a video monitor. Using this type of fluorescence imaging display for autofluorescence or endogenous tissue fluorescence imaging, areas of tissue in which the green fluorescence is suppressed due to abnormal pathology will appear red since the red fluorescence is proportionally less suppressed.

The processor/controller circuit 14 can carry out inter-image computation for superimposing a fluorescence image and a white-light light image on video monitor 18. An operator can therefore view the fluorescence image and the white-light light image simultaneously, without introducing a perceptible time delay between them. Consequently, for example, the location of a lesion can be readily viewed with high precision, which is very useful for diagnosis.

Figure 9:
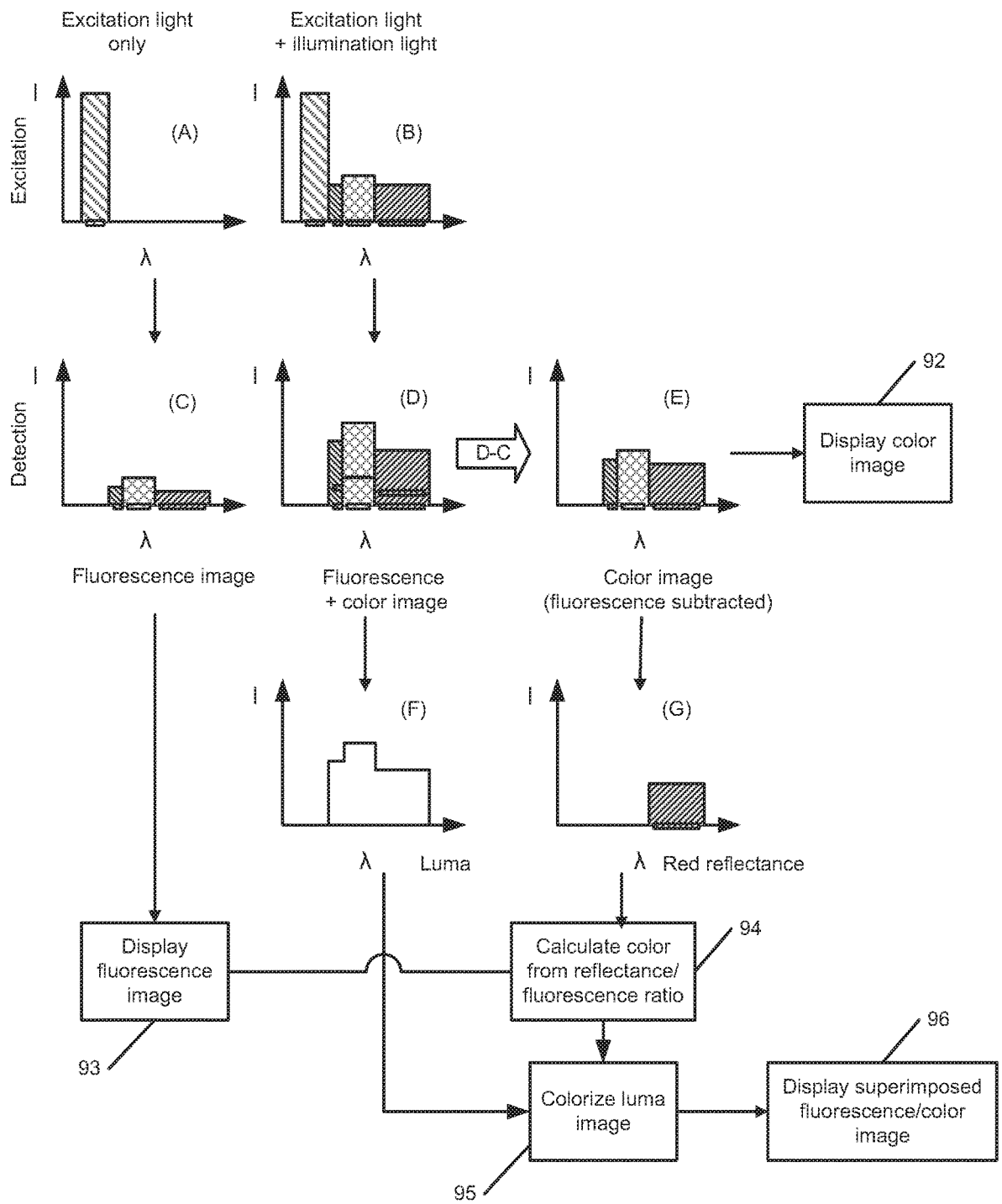
FIG. 9 shows schematically block diagram of a process according to the invention for extracting fluorescence and color images.

FIG. 9 illustrates schematically a process flow which may be performed, for example, by processor/controller 14, to extract fluorescence images and reflectance images, and to correct image intensity and color information for improving spatial resolution and for simultaneously displaying fluorescence/reflectance images.

The depicted process assumes that the excitation light, labeled (A) in FIG. 9, is emitted in the blue/UV spectral range, for example, for exciting fluorescence in fluorescein, which is detected in the green spectral range. However, other fluorescent dyes such as ICG which has excitation/fluorescence wavelengths in the red/IR spectral range can also be used, and the present invention is not limited to particular fluorescent materials or wavelengths. Illumination light is emitted at wavelengths outside the excitation light wavelengths and is shown together with the excitation light in FIG. 9 as (B).

When the tissue is illuminated with fluorescence light only, e.g., during the time interval between $T_0$ and $T_1$ (FIG. 7), a fluorescence spectrum (C) is detected by color sensor 22. When the tissue is illuminated with fluorescence light+ illumination light, e.g., in the time interval between $T_1$ and $T_2$ (FIG. 7), a fluorescence+color image spectrum (D) is detected by color sensor 22. The fluorescence spectrum (C) is then subtracted from the fluorescence+color image spectrum (D) to produce the spectral response of the color image (E). This color image can then be displayed at 92.

Advantageously, the "luma" component of the fluorescence+color image is extracted, shown as (F). Luma refers to the brightness in an image, i.e., the not-gamma-corrected "black and white" or achromatic portion of the image. Stated differently, luma represents the achromatic image without any color, while the chroma components represent the color information. The luma component can be used for extracting more accurate spatial information from the image data.

In one embodiment, the red reflectance signal (G) is extracted from the color image frames. A ratio of fluorescence to red reflectance for spatially corresponding pixels in the fluorescence and color video frames is calculated, at 94, on a pixel-by-pixel basis, and the value of that ratio is used to determine the color (chroma) of the display pixel at that same location, at 94. The color of a display pixel is assigned such that ratio values that indicate suppressed green fluorescence and abnormal pathology are rendered in a contrasting color to pixels in which the ratio values are characteristic of normal green fluorescence values indicating normal tissue pathology. Although the color (chroma) of the display pixels is based upon a ratio of fluorescence to reflectance signal for that pixel, the brightness (luma) of each display pixel may simply be taken as the brightness (luma) of each color video frame pixel. Because the color, or white-light, video fields are updated at near video rates (i.e. 4 times in a 6 field period, see FIGS. 7 and 8), the resulting fluorescence/reflectance image brightness defining the luma will also be updated at that rate. Conversely, the chroma portion of the fluorescence/reflectance image will be updated somewhat more gradually (due to the less frequent field update rate of the fluorescence image signals). However, the human eye is less sensitive to changes in color than to changes in brightness, so that the slower fluorescence field update rate will be less objectionable in the image display and can still be regarded as a real-time image. The luma image (F) can then be colored according to the chroma information derived from the red reflectance (G).

Normalizing a fluorescence image by a red light image is advantageous, because the color of mucosa inside a human body is dominated by hemoglobin which is a pigment and predominantly absorbs light with wavelengths shorter than 600 nm. The reference image used for normalization should therefore represent reflected wavelengths of 600 nm or longer. The normalized fluorescence image can then be used as an accurate representation of the intensity of actual fluorescence or the degree of accumulation of an antibody labeled, for example, by indocyanine green (ICG). Normalization of a fluorescence image is not limited to normalization relative to a red light image. Alternatively, an image depicted by infrared fluorescence components may be used for the normalization.

It should be mentioned that for removing excitation light, the excitation light blocking filter 24 in FIG. 2 may be replaced by a dichroic mirror which reflects the spectral components of the excitation light.

Recent developments in solid state lighting technology have given rise to the use of solid state devices, such as light-emitting diodes (LEDs) and lasers, as sources of endoscopic illumination which may eventually replace the lamps 31 and 32 in the multimode light source 12. Since LEDs are very compact, inexpensive, reliable, and have a long lifetime (on the order of 10,000 hours or longer, depending on the drive current), incorporation of this illumination technique in endoscopic medical equipment will lead to lower cost endoscopic light sources and hence also to less expensive endoscopes.

Solid state illumination sources, in particular LEDs, with emission wavelengths ranging from the deep UV to the infrared spectral range, have recently become available. These LEDs have several advantages which makes them particularly suitable for endoscopy: they can be manufactured to have a narrow, controllable spectral emission range which may be tuned to the fluorescence excitation spectra of the fluorophors; they are very efficiently in converting electric input power to optical output power; they can be rapidly switched on and off; and their power output can be adjusted by varying the electric current through the device which facilitates control and timing of the spectral output of an LED-based illumination source.

Figure 10A:
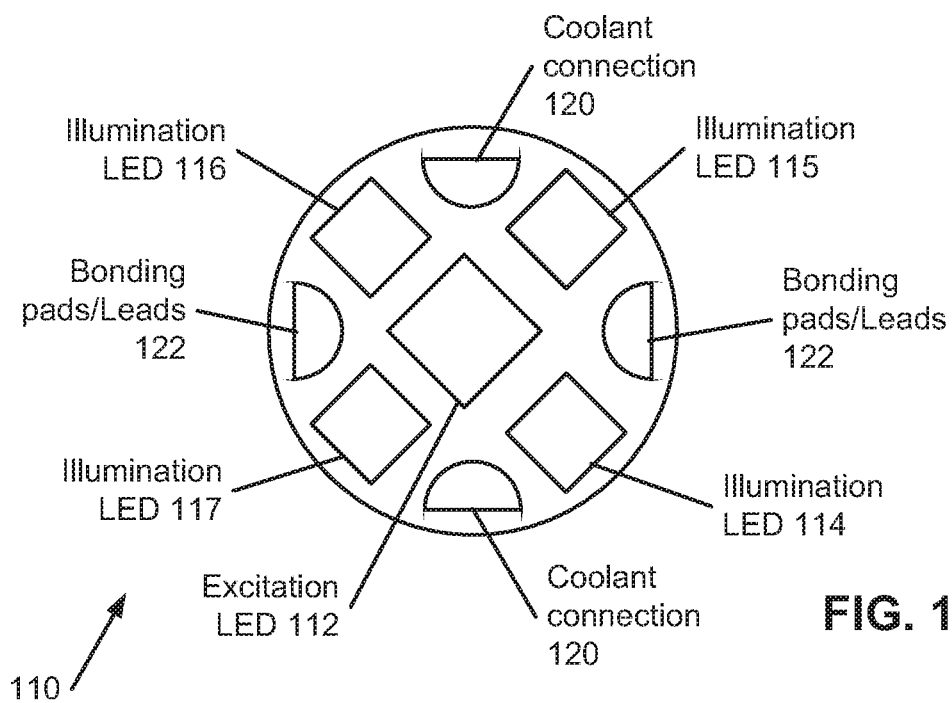
FIGS. 10A and 10B illustrate an LED assembly configured as a multi-wavelength illumination source for endoscopy.
Figure 10B:
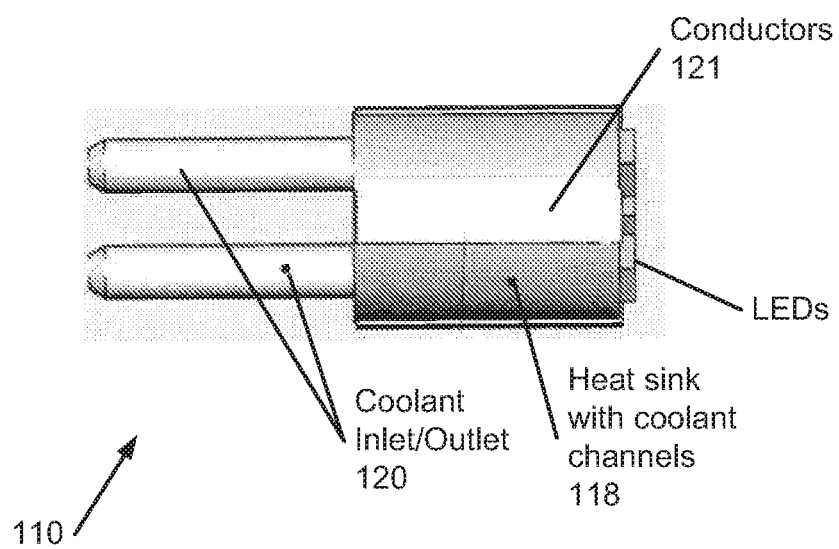

Due to their small die size, LEDs may be disposed at or incorporated in the distal tip of an endoscope. For example, as shown schematically in FIGS. 10A and 10B, several LEDs mounted on a common carrier can provide both narrow-band shorter wavelength excitation light for fluorescence endoscopy and broader visible illumination light for white-light endoscopy. FIG. 10A is a schematic top view of an illumination assembly 110 with an excitation, e.g. UV LED 112 die for providing excitation light, which is surrounded by blue (CWL 470 nm), green (CWL 525 nm), (CWL 590 nm) amber and red (CWL 630 nm) LED dies 114, 115, 116, 117 that provide illumination light. The indicated wavelengths are exemplary only and not intended to limit the scope of the invention. Also indicated are bonding pads 122 to electrically connect the LEDs to external wires (not shown). In general, more than the two indicated bonding pads may be provided. Each of the LEDs may be controlled individually.

In another embodiment not shown in the drawings, a so-called "white" LED which generates illumination light covering the visible spectral range can be employed instead of separate blue, green, red, and amber LEDs. "White" LEDs convert blue or UV radiation emitted by the blue- or UV-emitting LED die to visible light by down-conversion of the blue- or UV-emission with a suitable phosphor. Both types of LEDs have recently become commercially available. Advantageously, the LEDs can be lensed for efficient directional illumination of the target tissue. The excitation LED may emit light in any spectral range suitable for exciting fluorescence in a dye, such as in the blue for fluorescein and in the near IR for ICG.

It will be understood that light emitted by the illumination LEDs should not contain spectral components in a wavelength range where dye fluorescence is excited. To eliminate emission at excitation light wavelengths from reaching the tissue under examination, suitable cutoff or pass-band, for example notch filters, may be placed in the optical path of the separate color LEDs or the "white-light" LEDs of illumination assembly 110.

Although LEDs convert electric energy to optical energy very efficiently, they still generate a substantial amount of heat which may cause discomfort for the patient. These LEDs may therefore have to be cooled. As shown more clearly in FIG. 10B, the LEDs may be mounted on a heat sink 118 with a coolant inlet/outlet which can be connected to an external chiller. In general, devices for cooling the LEDs may include thermoelectric coolers, liquid-cooled heat exchangers, expansion coolers, microchannel coolers, thermosiphon heat pipes, and the like.

The excitation light blocking filter 24 for the excitation light placed in front of the sensor may be designed to prevent transmission of blue or UV light produced by the white-light LED. Alternatively or in addition, the LED itself may be covered with a filter absorbing the blue or UV light from the LED dies.

A temperature sensor may be incorporated into the heat sink 118, or mounted in close vicinity to the LED array, for the purposes of 1. monitoring and adjusting the heat sink temperature, and
2. providing a safety mechanism by which a signal can be generated to reduce or interrupt the electrical power to the LEDs in the event of a failure in the heat sink cooling system.

While the invention has been disclosed in connection with the preferred embodiments shown and described in detail, various modifications and improvements thereon will become readily apparent to those skilled in the art. For example, although not illustrated in the drawings, the illumination sources, such as the arc lamp or halogen lamp, may be replaced with LEDs or lasers. Accordingly, the spirit and scope of the present invention is to be limited only by the following claims.

The invention claimed is:

1. A method of visualizing a tissue of a subject, the method comprising:
   illuminating the tissue with white-light and excitation light that excites fluorophors in the tissue, wherein the fluorophors emit fluorescence light to create a fluorescence image;
   simultaneously receiving visible white-light image data and corresponding fluorescence image data of the tissue, the visible white-light image data and the fluorescence image data being captured or having been captured by an image capture device;
   colorizing the visible white-light image data based on the fluorescence image data to generate a composite colorized image, wherein the composite colorized image comprises a plurality of differentiated color regions, the differentiated color regions corresponding to a change in fluorescence signal from the tissue, and wherein a brightness of the composite colorized image data is based on white-light image data and is independent of the fluorescence image data; and
   displaying the composite colorized image.

2. The method of claim 1, wherein the change in fluorescence signal is indicative of a change in a property of the tissue.

3. The method of claim 2, wherein the property of the tissue is indicative of tissue health.

4. The method of claim 2, wherein the property of the tissue comprises a pathological property.

5. The method of claim 2, wherein the property of the tissue comprises a structural property.

6. The method of claim 1, wherein colorizing the visible white-light image data based on the fluorescence image data comprises modifying a color attribute of the visible white-light image data.

7. The method of claim 1, wherein the visible white-light image data comprises desaturated image data.

8. The method of claim 1, wherein the visible white-light image data comprises grayscale image data.

9. The method of claim 1, wherein the visible white-light image data comprises luma image data.

10. A system for visualizing a tissue of a subject, the system comprising:
    one or more light sources for illuminating the tissue;
    one or more image sensors for simultaneously detecting a visible white-light image and a fluorescence image;
    one or more processors configured to compute a composite colorized image using the detected visible white-light image and the detected fluorescence image, wherein the composite colorized image comprises a plurality of differentiated color regions, the differentiated color regions corresponding to a change in fluorescence signal from the tissue, and wherein a brightness of the composite colorized image data is based on white-light image data and is independent of the fluorescence image data; and
    a display for displaying the composite colorized image.

11. The system of claim 10, wherein the system is an endoscope system.

12. The system of claim 10, wherein the one or more image sensors comprise one or more CCD or CMOS image sensors.

13. The system of claim 10, comprising a single sensor for detecting the white-light image and the fluorescence image.

14. The system of claim 10, wherein the change in fluorescence signal is indicative of a change in a property of the tissue.

15. The system of claim 14, wherein the property of the tissue is indicative of tissue health.

16. The system of claim 14, wherein the property of the tissue comprises a pathological property.

17. The system of claim 14, wherein the property of the tissue comprises a structural property.

18. The system of claim 10, wherein the composite colorized image is computed by colorizing visible white-light image data based on fluorescence image data.

19. The system of claim 18, wherein the visible white-light image data is colorized based on fluorescence image data by modifying a color attribute of the visible white-light image data based on the fluorescence image data.

20. The system of claim 18, wherein the visible white-light image data comprises desaturated image data.

21. The system of claim 18, wherein the visible white-light image data comprises luma image data.

22. The system of claim 18, wherein the visible white-light image data comprises grayscale image data.

23. The method of claim 1, further comprising administering a fluorescent dye to the subject comprising indocyanine green (ICG).

* * * * *